(12) United States Patent
Wilkison et al.

(10) Patent No.: US 11,596,644 B2
(45) Date of Patent: Mar. 7, 2023

(54) METHOD FOR TREATING POST-PRANDIAL HYPOGLYCEMIA

(71) Applicants: AVOLYNT, Research Triangle Park, NC (US); KISSEI PHARMACEUTICAL CO., LTD., Nagano-Prefecture (JP)

(72) Inventors: William Wilkison, Raleigh, NC (US); Bentley Cheatham, Durham, NC (US); James T. Green, Raleigh, NC (US)

(73) Assignees: AVOLYNT, Research Triangle, NC (US); KISSEI PHARMACEUTICAL CO., LTD., Nagano-Prefecture (JP)

( * ) Notice: Subject to any disclaimer, the term of this patent is extended or adjusted under 35 U.S.C. 154(b) by 0 days.

(21) Appl. No.: 17/041,577

(22) PCT Filed: Mar. 28, 2019

(86) PCT No.: PCT/US2019/024463
§ 371 (c)(1),
(2) Date: Sep. 25, 2020

(87) PCT Pub. No.: WO2019/191352
PCT Pub. Date: Oct. 3, 2019

(65) Prior Publication Data
US 2021/0085701 A1    Mar. 25, 2021

Related U.S. Application Data

(60) Provisional application No. 62/649,352, filed on Mar. 28, 2018.

(51) Int. Cl.
| | | |
|---|---|---|
| A61K 31/706 | (2006.01) | |
| A61K 31/7056 | (2006.01) | |
| A61P 3/08 | (2006.01) | |
| A61K 31/702 | (2006.01) | |

(52) U.S. Cl.
CPC .......... *A61K 31/706* (2013.01); *A61K 31/702* (2013.01); *A61K 31/7056* (2013.01); *A61P 3/08* (2018.01)

(58) Field of Classification Search
CPC .............................. A61K 31/7056; A61P 3/08
See application file for complete search history.

(56) References Cited

U.S. PATENT DOCUMENTS

| | | | |
|---|---|---|---|
| 7,635,684 B2 | 12/2009 | Fushimi et al. | |
| 8,324,176 B2 * | 12/2012 | Fushimi | A61P 3/08 |
| | | | 536/17.4 |
| 8,354,382 B2 | 1/2013 | Takeuchi et al. | |
| 8,399,418 B2 | 3/2013 | Takeuchi et al. | |
| 9,200,025 B2 | 12/2015 | Carson et al. | |
| 9,694,027 B2 | 7/2017 | Isaji et al. | |
| 2011/0218159 A1 * | 9/2011 | Brown | A61P 3/06 |
| | | | 514/24 |
| 2015/0005233 A1 | 1/2015 | Defrees | |

OTHER PUBLICATIONS

Beshyah, Salem, Ibnosina Journal of Medicine and Biomedical Sciences, "First Beneficial Use of Dapagliflozin for Treatment of Post-Bariatric Hypoglycemia: Case Report and Hypothesis", 2016, vol. 8, No. 6, pp. 335-342 (Year: 2016).*
Inoue, Toshihiro et al., European Journal of Pharmacology, "Mizagliflozin, a novel selective SGTL1 inhibitor, exhibits potential in the amelioration of chronic constipation", 2017, vol. 806, pp. 25-31 (Year: 2017).*
Powell, David R. et al., The Journal of Pharmacology and Experimental Therapeutics, "LX2761, a Sodium/Glucose Cotransporter 1 Inhibitor Restricted to the Intestine, Improves Glycemic Control in Mice", 2017, vol. 362, pp. 85-97 (Year: 2017).*
Sands, Arthur T. et al., Diabetes Care, "Sotagliflozin, a Dual SGLT1 and SGLT2 inhibitor, as adjunct therapy to insulin in type 1 diabetes", 2015, vol. 38, pp. 1181-1188 (Year: 2015).*
International Search Report and Written Opinion in International Application No. PCT/US2019/024463, dated Jun. 11, 2019.
International Preliminary Report on Patentability in International Application No. PCT/US2019/024463, dated Oct. 8, 2020.
Dobbins et al., "Selective sodium-dependent glucose transporter 1 inhibitors blocl glucose absorption and impair glucose-dependent insulinotropic peptide release", Am. J. Physiol. Gastrointest. Liver Physiol. 308; G946-G954, 2015.
Powell et al., "LX2761, a Sodium/Glucose Cotransporter 1 inhibitor Restricted to the Intestine, Improves Glycemic Control in Mice", J. Pharmacol. Exp. Ther. 362:85-97, 2017.
Shibazaki et al., "KGA-2727, a Novel Selective Inhibitor of a High Affinity Sodium Glucose Cotransporter (SGLT1), Exhibits Antidiabetic Efficacy in Rodent Models", Journal of Pharmacology and Experimental Therapeutics; vol. 342, No. 2, pp. 288-296.
Fushimi et al., :"Structure-activity relationship studies of 4-benzyl-1H-pyrazol-3-yl [beta]-d-glucopyranoside derivatives as potent and selective sodium glucose co-transporter 1 (SGLT1) inhibitors with therapeutic activity on postprandial hyperglycemia", Bioorganic, vol. 20, No. 22, pp. 6598-6612.
Sands et al., "Sotagliflozin, a Dual SGLT 1 and SGLT2 Inhibitor, as Adjunct Therapy to Insulin in Type 1 Diabetes", Diabetes Care, vol. 38, No. 7, pp. 1181-1188.
Goldfine et al., "Patients with Neuroglycopenia after Gastric Bypass Surgery Have Exaggerated Incretin and Insulin Secretory Responses to a Mixed Meal", Journal of Clinical Endocrinology and Metabolism, vol. 92, No. 12, pp. 4678-4685.
Salehi et al., "Blockade of Glucagon-like Peptide 1 Receptor Corrects Postprandial Hypoglycemia After Gastric Bypass", Gastroenterology, vol. 146, No. 3, Mar. 1, 2014 (Mar. 1, 2014), pp. 669-680.
Goodwin et al., "Discovery of LX2761, a Sodium-Dependent Glucose Cotransporter 1 (SGLTI) Inhibitor Resfticted to the Intestinal Lumen, for the Treatment of Diabetes", Journal of Medicinal Chemistry, vol. 60, No. 2, pp. 710-721.

(Continued)

*Primary Examiner* — Bahar Craigo
(74) *Attorney, Agent, or Firm* — Raphael Bellum PLLC

(57) ABSTRACT

Disclosed herein are methods, sodium-dependent glucose transporter (SGLT)1 compounds and compositions for the treatment of postprandial hypoglycemia, postprandial hypoglycemia that occurs as a consequence of gastric surgery.

15 Claims, 22 Drawing Sheets

(56) References Cited

OTHER PUBLICATIONS

Extended European Search Report in Application No. 19776303.0, dated Jan. 17, 2022.

* cited by examiner

METHOD FOR TREATING POST-PRANDIAL HYPOGLYCEMIA

FIELD OF THE INVENTION

The invention relates to methods and compositions for the treatment of post-prandial hypoglycemia associated with gastric surgery.

BACKGROUND

Post-prandial hypoglycemia (PPH) has been observed as a side effect or complication of gastric surgery, such as gastric bypass surgery. A commonly observed side effect of gastric bypass surgery is dumping, which is consequence of the ingestion of simple sugars and rapid emptying of food into the small intestine. Early dumping occurs 10 to 30 minutes after a meal. It results from rapid movement of fluid into the intestine following a sudden addition of a large amount of food from the stomach. The small intestine expands rapidly due to the presence of hypertonic/hyperosmolar contents from the stomach, especially sweet foods. This causes symptoms due to the shift of fluid into the intestinal lumen, with plasma volume contraction and acute intestinal distention. Late dumping can occur up to a few hours after eating and results from insulin response to hyperglycemia resulting from rapid absorption of simple sugars from the proximal small intestine. Late dumping occurs 2 to 3 hours after a meal. It results from excessive movement of sugar into the intestine, which raises the body's blood glucose level and causes the pancreas to increase its release of the hormone insulin. The increased release of insulin causes a rapid drop in blood glucose levels, a condition known as alimentary hypoglycemia, or low blood sugar.

Post-prandial hypoglycemia is also a frequent complication of Nissen fundoplication, a procedure commonly performed to treat severe gastroesophageal reflux. Up to 30% of patients undergoing this procedure develop dumping syndrome. Dumping syndrome is characterized by early symptoms or "early dumping" due to the fluid shifts provoked by the osmotic load in the small bowel and "late dumping" or post-prandial hypoglycemia. See Zaloga GP, Chernow B. Postprandial hypoglycemia after Nissen fundoplication for reflux esophagitis. Gastroenterology. 1983; 84: 840-842; Bufler P, Ehringhaus C, Koletzko S. Dumping Syndrome: a common problem following Nissen fundoplication in young children. Pediatr Surg Int. 17 (5-6): 351-355, 2001; Samuk I, Afriat R, Horne T, Bistritzer T, Barr J, Vinograd I. Dumping syndrome following Nissen fundoplication, diagnosis and treatment. J Pediatr Gastroenterol Nutr. 1996; 23 (3): 235-240.

Postprandial hypoglycemia can occur in patients with gastric bypass surgery in the context of the dumping syndrome. (Singh et al., Diabetes Spectrum 2012 Nov.; 25(4): 217-221. Dumping can occur postoperatively in up to half of gastric bypass patients with ingestion of simple sugars. Id. Early dumping, a result of rapid emptying of food into the jejunum because of the surgically altered anatomy, is characterized by vasomotor symptoms (flushing, tachycardia), abdominal pain, and diarrhea. Id. Late dumping, a form of "reactive hypoglycemia," occurs 1-3 hours after meal ingestion and is a consequence of the brisk insulin response to hyperglycemia resulting from rapid absorption of simple sugars from the proximal small intestine. Id. These patients present with dizziness, fatigue, weakness, and diaphoresis, but these symptoms often resolve spontaneously and neuroglycopenic symptoms may not be prominent. Id. Most patients with dumping syndrome respond to nutrition modification, comprising frequent, small, and low-carbohydrate meals. Id. Pharmacological therapy is sometimes necessary. Id. Acarbose and somatostatin have also been empirically associated with improvement of symptoms in some patients, but the primary modality of treatment of these patients is still nutrition intervention, and pharmacotherapy is used as an add-on intervention only. Id. Indeed, the use of acarbose in patients who are not compliant with nutrition recommendations can be expected to have significant gastrointestinal side effects. Id.

An effective pharmacotherapy treatment of post-prandial hypoglycemia associated with gastric surgeries, which does not also necessarily require patient compliance with strict nutritional modifications would address a long-standing need for a convenient alternative PPH therapy. In that regard, inhibiting absorption of carbohydrates, such as glucose, at the small intestine, by blocking sodium-dependent glucose transporter (SGLT) activity subsequently can prevent an increase of blood sugar level, and, thereby, reduce or prevent the occurrence of PPH.

Subtypes of SGLT include SGLT1, which is primarily expressed in the small intestine, and SGLT2, which is expressed in the renal proximal tubule. These are responsible for absorption of glucose in the small intestine and reabsorption of glucose in the proximal tubule. U.S. Pat. No. 7,635,684, herein incorporated by reference in its entirety, describes compounds that show an inhibitory activity in human SGLT1 at the small intestine. U.S. Pat. No. 9,200,025, herein incorporated by reference in its entirety, describes potent inhibitors of SGLT1, with particular inhibitors selective inhibitors for SGLT1, and particular inhibitors having low systemic exposure, and act locally in the gut.

Mizagliflozin, 3-(3-{4-[3-($\beta$-D-glucopyranosyloxy)-5-isopropyl-1H-pyrazol-4-ylmethyl-]-3-methylphenoxy}propylamino)-2,2-dimethylpropionamide, is a SGLT1 inhibitor created by Kissei Pharmaceutical Co., Ltd. No SGLT1 inhibitors have been approved to date. Mizagliflozin suppresses the uptake of glucose from the digestive tract by selectively inhibiting SGLT1. In addition, it acts primarily in the upper part of the small intestine and has a weak inhibitory effect on glucose absorption in the lower part of the small intestine since it is broken down and deactivated as it moves through the digestive tract. Gastrointestinal symptoms are not readily likely if the amount of glucose that remains without being absorbed is small.

Since an increase of SGLT1 activity in the small intestine is thought to contribute to increased carbohydrate absorption, fast development of agents, which have a potent inhibitory activity in human SGLT1, has been desired for the prevention or treatment of diabetes. See e.g., U.S. Pat. No. 8,324,176. Crystalline compounds of mizagliflozin have been described for use of prevention or treatment of a disease associated with hyperglycemia such as diabetes, impaired glucose tolerance, impaired fasting glycemia, diabetic complications or obesity, and a disease associated with the increase in blood galactose level such as galactosemia. U.S. Pat. No. 8,399,418 describes the monosebacate salt of mizagliflozin, and U.S. Pat. No. 8,354,382 describes the hemifumarate dehydrate salt of mizagliflozin. U.S. Pat. No. 9,694,027 describes the use of Mizagliflozin to treat constipation.

SUMMARY OF THE INVENTION

The invention relates to methods and compositions for the treatment of post-prandial hypoglycemia associated with gastric surgery. In particular, methods of the invention relate to treating a subject with post-prandial hypoglycemia associated with a gastric surgery, comprising the step of orally administering a SGLT1 inhibitor compound of Formula I or II, or a pharmaceutically acceptable salt thereof, to said subject, wherein the compound of Formula I is:

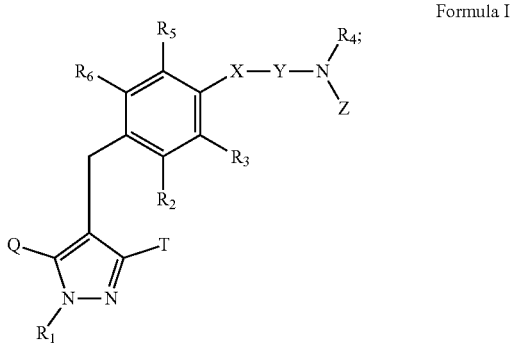

Formula I wherein $R_1$ represents H, or an optionally substituted $C_{1-6}$ alkyl group;

one of Q and T represents a group:

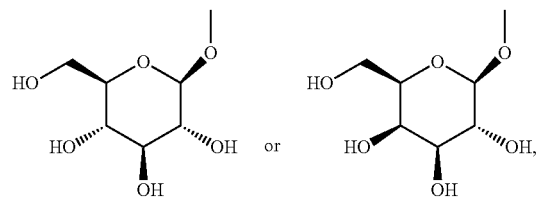

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R_2$ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or -A-$R^A$ in which A represents a single bond, an oxygen atom, a methylene group, an ethylene group, —OCH$_2$— or —CH$_2$O—; and $R^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

Y represents a $C_{1-6}$ alkylene group which may be substituted by a hydroxy group or a $C_{2-6}$ alkenylene group;

Z represents —$R^B$, —COR$^C$, —SO$_2$R$^C$, —CON(R$^D$)R$^E$, —SO$_2$NHR$^F$ or —C(=NR$^G$)N(R$^H$)R$^I$; R$^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i);

$R_4$, $R^B$, $R^D$, $R^E$ and $R^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), or both of $R_4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group; $R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i), or both of $R^G$ and $R^H$ bind to form an ethylene group, or both of $R^H$ and $R^I$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R_3$, $R_5$ and $R_6$ are the same or different, and each represents a hydrogen atom, a halogen atom, a $C_{1-6}$ alkyl group or a $C_{1-6}$ alkoxy group;

and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy ($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON(R$^J$)R$^K$ in which R$^J$ and R$^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy ($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of RJ and RK bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent;

and wherein the compound of Formula II is:

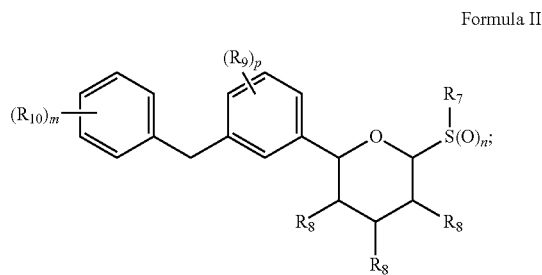

Formula II wherein $R_7$ is hydrogen or optionally substituted $C_{1-10}$-alkyl, $C_{1-5}$-cycloalkyl, or 5-membered heterocycle, which optional substitution is with one or more $R_{7A}$; each $R_{7A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{7B}$; each $R_{7B}$ is independently $C_{1-4}$-alkyl, halo, or hydroxyl; n is 0, 1, or 2;

each $R_8$ is independently F or $OR_{8A}$, wherein each $R_{8A}$ is independently hydrogen, $C_{1-4}$-alkyl, or acyl;

each $R_9$ is independently halo, hydroxyl, or optionally substituted $C_{1-10}$-alkyl or $C_{1-10}$-alkoxy, which optional substitution is with one or more $R_{9A}$; each $R_{9A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{9B}$; each $R_{9B}$ is independently $C_{1-4}$-alkyl, amino, cyano, halo, or hydroxyl;

p is 0, 1, or 2;

each $R_{10}$ is independently $R_{10A}$, —$N(R_{10A})(R10B)$, —$OR_{10A}$, —$SR_{10A}$, —$S(O)R_{10A}$, or —$S(O)_2R_{10A}$; $R_{10A}$ is optionally substituted $C_{4-20}$-alkyl or 4-20-membered heteroalkyl, which optional substitution is with one or more $R_{10C}$, and which is optionally attached to another $R_{10A}$ moiety to provide a dimer or trimer; $R_{10B}$ is hydrogen or $R_{10A}$; each $R_{10C}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, thiourea, urea, or $X_1$, $X_1$-$L_1$-$X_2$, or $X_1$-$L_1$-$X_2$-$L_2$-$X_3$, wherein each of $X_1$, $X_2$ and $X_3$ is independently optionally substituted $C_{1-4}$-alkyl, $C_{1-6}$-cycloalkyl, 5- or 6-membered heterocycle, or aryl, which optional substitution is with one or more $R_{10D}$, and each of $L_1$ and $L_2$ is independently optionally substituted $C_{1-6}$-alkyl or 1-10-membered heteroalkyl, which optional substitution is with one or more of $R_{10E}$; each $R_{10D}$ is independently $R_{10E}$ or $C_{1-6}$-alkyl optionally substituted with one or more of $R_{10E}$; each $R_{10E}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, or urea; and m is 1, 2 or 3; wherein the SGLT1 inhibitor compound inhibits SGLT1 in the intestinal lumen of the subject.

DETAILED DESCRIPTION

Figure 1A:
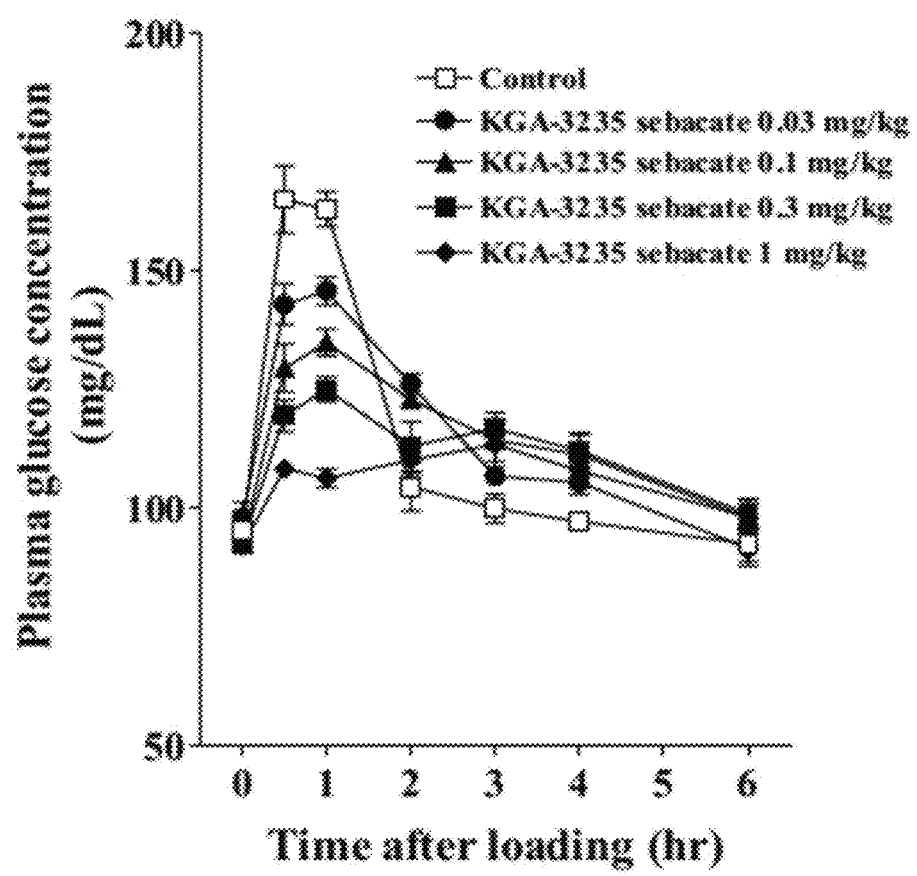
FIG. 1(A-B) shows effects of a single dose of mizagliflozin, referred to as KGA-3235 sebacate, and voglibose on plasma glucose levels in normal rats following mixed carbohydrate load.

The invention generally relates to methods of treatment of post-prandial hypoglycemia by administering SGLT1 inhibitor compounds. In particular, the invention relates to a method of treating a subject with post-prandial hypoglycemia associated with a gastric surgery, comprising the step of orally administering a SGLT1 inhibitor compound of Formula I or II, or a pharmaceutically acceptable salt thereof to said subject, wherein the compound of Formula I is:

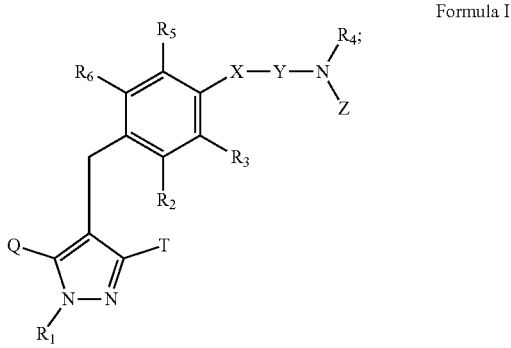

Formula I wherein $R_1$ represents H, or an optionally substituted $C_{1-6}$ alkyl group;

one of Q and T represents a group:

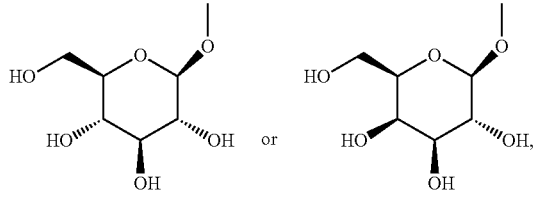

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;

$R_2$ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or -A-$R^A$ in which A represents a single bond, an oxygen atom, a methylene group, an ethylene group, —OCH$_2$— or —CH$_2$O—; and $R^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;

X represents a single bond, an oxygen atom or a sulfur atom;

Y represents a $C_{1-6}$ alkylene group which may be substituted by a hydroxy group or a $C_{2-6}$ alkenylene group;

Z represents —$R^B$, —COR$^C$, —SO$_2$R$^C$, —CON(R$^D$)R$^E$, —SO$_2$NHR$^F$ or —C(=NR$^G$)N(R$^H$)R$^I$; R$^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i);

$R_4$, $R^B$, $R^D$, $R^E$ and $R^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), or both of $R_4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group; $R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i), or both of $R^G$ and $R^H$ bind to form an ethylene group, or both of $R^H$ and $R^I$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group;

$R_3$, $R_5$ and $R_6$ are the same or different, and each represents a hydrogen atom, a halogen atom, a $C_{1-6}$ alkyl group or a $C_{1-6}$ alkoxy group;

and substituent group (i) consists of a hydroxy group, a $C_{1-6}$ alkoxy group, a $C_{1-6}$ alkylthio group, an amino group, a mono or di($C_{1-6}$ alkyl)amino group, a mono or di[hydroxy ($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON(R$^J$)R$^K$ in which R$^J$ and R$^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy ($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of RJ and RK bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent;

and wherein the compound of Formula II is:

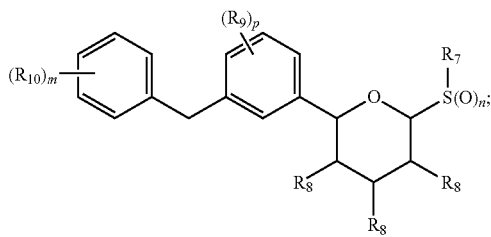

Formula II wherein $R_7$ is hydrogen or optionally substituted $C_{1-10}$-alkyl, $C_{1-5}$-cycloalkyl, or 5-membered heterocycle, which optional substitution is with one or more $R_{7A}$; each $R_{7A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{7B}$; each $R_{7B}$ is independently $C_{1-4}$-alkyl, halo, or hydroxyl; n is 0, 1, or 2;

each $R_8$ is independently F or $OR_{8A}$, wherein each $R_{8A}$ is independently hydrogen, $C_{1-4}$-alkyl, or acyl;

each $R_9$ is independently halo, hydroxyl, or optionally substituted $C_{1-10}$-alkyl or $C_{1-10}$-alkoxy, which optional substitution is with one or more $R_{9A}$; each $R_{9A}$ is independently amino, ester, amide, thiol, carboxylic acid, cyano, halo, hydroxyl, or optionally substituted $C_{1-4}$-alkoxy, $C_{1-5}$-cycloalkyl, or 5-membered heterocycle, which optional substitution is with one or more $R_{9B}$; each $R_{9B}$ is independently $C_{1-4}$-alkyl, amino, cyano, halo, or hydroxyl;

p is 0, 1, or 2;

each $R_{10}$ is independently $R_{10A}$, —N($R_{10A}$)(R10B), —$OR_{10A}$, —$SR_{10A}$, —$S(O)R_{10A}$, or —$S(O)_2R_{10A}$; $R_{10A}$ is optionally substituted $C_{4-20}$-alkyl or 4-20-membered heteroalkyl, which optional substitution is with one or more $R_{10C}$, and which is optionally attached to another $R_{10A}$ moiety to provide a dimer or trimer; $R_{10B}$ is hydrogen or $R_{10A}$; each $R_{10C}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, thiourea, urea, or $X_1$, $X_1$-$L_1$-$X_2$, or $X_1$-$L_1$-$X_2$-$L_2$-$X_3$, wherein each of $X_1$, $X_2$ and $X_3$ is independently optionally substituted $C_{1-4}$-alkyl, $C_{1-6}$-cycloalkyl, 5- or 6-membered heterocycle, or aryl, which optional substitution is with one or more $R_{10D}$, and each of $L_1$ and $L_2$ is independently optionally substituted $C_{1-6}$-alkyl or 1-10-membered heteroalkyl, which optional substitution is with one or more of $R_{10E}$; each $R_{10D}$ is independently $R_{10E}$ or $C_{1-6}$-alkyl optionally substituted with one or more of $R_{10E}$; each $R_{10E}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, or urea; and m is 1, 2 or 3; wherein the SGLT1 inhibitor compound inhibits SGLT1 in the intestinal lumen of the subject.

The SGLT1 inhibitor compounds of Formula I or Formula II administered in methods of the invention inhibit SGLT1 in the intestinal lumen of the subject. Accordingly, the SGLT1 inhibitor compounds of Formula I or Formula II are locally acting in the gut, and have poor systemic exposure. Particular locally acting compounds have a maximum plasma concentration ($C_{max}$) of less than 250, 100, 50, or 10 nM when orally administered at a dose of 10 mg/kg to a mouse, rat or human. Systemic exposure (e.g., $C_{max}$) can be measured by methods well known in the art, including liquid chromatography mass spectrometry. For example, after oral administration of mizagliflozin at doses of 3, 10, and 30 mg/kg to fasted male rats, exposure of mizagliflozin, maximal observed concentration (Cmax) and the area under the plasma concentration versus time curve from time zero to last measurable concentration (AUCt) increased with dose, but not in a clear dose proportional manner. The oral bioavailability of mizagliflozin in the rat was very low (range 0.01 to 0.08%). The majority of mizagliflozin remains in the intestine after oral dosing and is excreted almost exclusively in the feces in rats (>97% of orally administered dose) and in non-human primates (>82% of orally administered dose).

"Pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., Remington's Pharmaceutical Sciences, 18$^{th}$ ed. (Mack Publishing, Easton Pa.: 1990) and Remington: The Science and Practice of Pharmacy, 19$^{th}$ ed. (Mack Publishing, Easton Pa.: 1995).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A "therapeutically effective amount" of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

The terms "treat," "treating," and "treatment" contemplate an action that occurs while a patient is suffering from the specified disease or disorder, which reduces the severity of the disease or disorder, or retards or slows the progression of the disease or disorder.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

Gastric surgery includes, but is not limited to gastric bypass surgery, esophageal surgery, vagotomy, and pyloroplasty. Non-limiting examples of gastric surgeries include gall bladder surgery, stomach cancer surgery (gastrectomy), colorectal cancer surgery, esophageal cancer surgery, inflammatory bowel disease surgery, Roux-en-Y, sleeve gastrectomy, biliopancreatic diversion, vertical banded gastroplasty and laparoscopic adjustable gastric banding. Nissen fundoplication is an esophageal surgery. Another esophageal surgery is esophagectomy. Reference for each of these as it relates to hypoglycemia is found in van Beek, A. P., Emous, M., Laville, M., and Tack, J. 2017 Obesity Reviews 18: 68-85.

In a preferred method of the invention, the postprandial hypoglycemia is associated with gastric bypass surgery. Gastric bypass surgery is a surgical procedure in which the stomach is divided into a small upper pouch and a much larger lower remnant pouch and then the small intestine is rearranged to connect to both.

In another preferred method of the invention, the postprandial hypoglycemia is associated with Nissen fundoplication. A Nissen fundoplication, or laparoscopic Nissen fundoplication when performed via laparoscopic surgery, is a surgical procedure to treat gastroesophageal reflux disease (GERD) and hiatal hernia. In a fundoplication, the gastric fundus (upper part) of the stomach is wrapped, or plicated, around the lower end of the esophagus and stitched in place, reinforcing the closing function of the lower esophageal sphincter. The esophageal hiatus is also narrowed down by sutures to prevent or treat concurrent hiatal hernia, in which the fundus slides up through the enlarged esophageal hiatus of the diaphragm. In a Nissen fundoplication, also called a complete fundoplication, the fundus is wrapped the entire 360 degrees around the esophagus. (https://en.wikipedia.org/wiki/Nissen_fundoplication, accessed Mar. 16, 2018.)

Postprandial hypoglycemia, in post gastric bypass surgery subjects and in subjects that have had a Nissen fundoplication, is a form of reactive hypoglycemia involving a characteristic hyperinsulinemic response. In these subjects, the hyperinsulinemic response is preceded by a significant increase in peak postprandial plasma glucose concentrations. As a potential effective therapy, SGLT1 compounds of Formula I and Formula II would inhibit glucose uptake in the intestine, reducing the postprandial rise in plasma glucose concentration and thereby inhibiting the hyperinsulinemic response and subsequent hypoglycemia. In a series of preclinical studies performed in normal rats, diabetic rats and in diet-induced obese marmosets, when administered prior to a meal challenge (oral glucose or mixed meal tolerance test), mizagliflozin significantly reduced the peak postprandial glucose concentration and the total $\Delta AUC_{0-1\ h}$. The preclinical data disclosed below demonstrate that mizagliflozin can prevent the postprandial spike in plasma glucose concentration that precedes the hyperinsulinemic response. In addition, clinical studies demonstrating the effect of mizagliflozin on postprandial glucose and insulin have also been conducted in healthy human volunteers and in subjects with type 2 diabetes (examples provided below). In these studies, subjects were administered mizagliflozin prior to an oral glucose tolerance or mixed meal tolerance test. Results from these clinical studies demonstrated that treatment with mizagliflozin, prior to a meal challenge, reduced the peak postprandial plasma glucose concentration and delayed the time to peak glucose concentration in a dose-dependent manner. Insulin displayed a similar postprandial profile to that of glucose, where peak plasma insulin concentrations were reduced and the time to peak insulin concentration delayed. These data are highly supportive of the ability of mizagliflozin to blunt the hyperglycemic hyperinsulinemic response and mitigate postprandial hypoglycemia.

As demonstrated in Examples 9 and 10, these various SGLT1 inhibitors (KGA2727, KGA2586, KGA2588, KGA2891 and LX2761) lowered blood glucose after administration of a mixed carbohydrate test (KGA compounds) or an oral glucose tolerance test (LX2761). This data is highly supportive of the ability of these SGLT1 inhibitors as being efficacious in lowering blood glucose in patients with post-bariatric hypoglycemia by virtue of their ability to blunt postprandial glucose absorption.

For the methods of the invention, SGLT1 inhibitors of Formula I and Formula II can be prepared by methods known in the art. See e.g., U.S. Pat. Nos. 7,635,684, and 9,200,025.

In a preferred method of the invention, SGLT1 inhibitors of Formula I and Formula II are selected from the group consisting of:

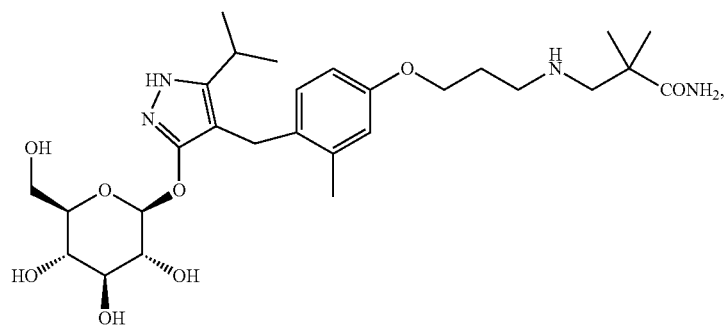
KGA-3235 Mizagliflozin
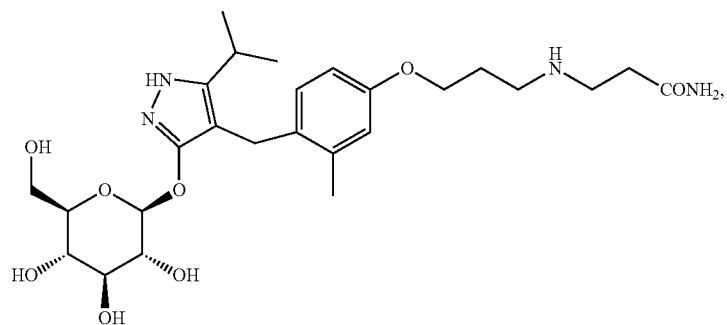
KGA-2727
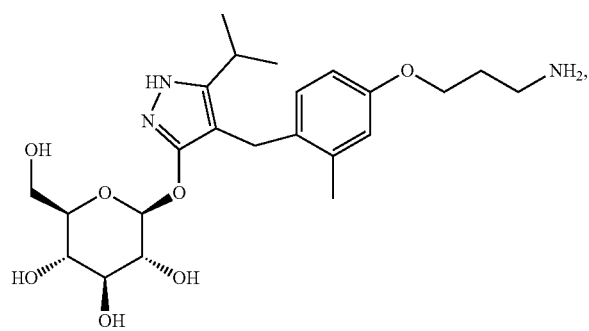
KGA-2586
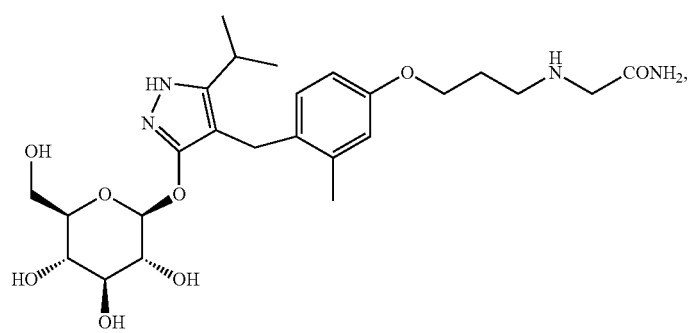
KGA-2588

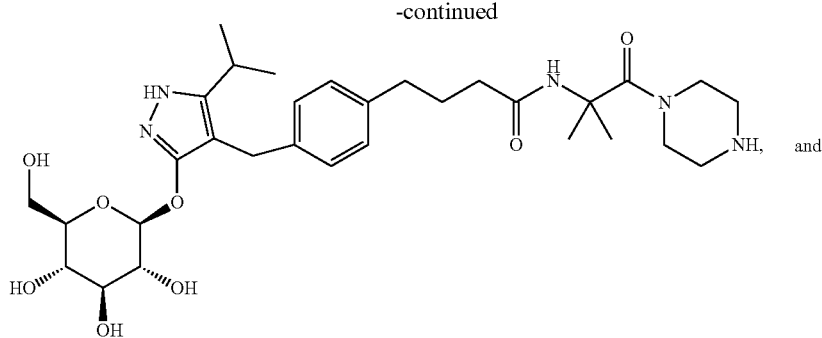

KGA-2891

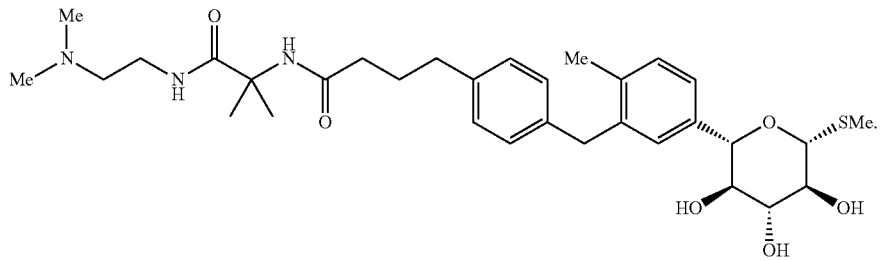

LX2761

In some preferred methods of the invention, the SGLT1 inhibitor is selected from LX2671 and mizagliflozin.

In an even more preferred method of the invention, the SGLT1 inhibitor is mizagliflozin. Mizagliflozin, 3-(3-{4-[3-(β-D-glucopyranosyloxy)-5-isopropyl-1H-pyrazol-4-ylmethyl-]-3-methylphenoxy}propylamino)-2,2-dimethylpropionamide, can be converted to a pharmaceutically acceptable salt according to methods known in the art. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, glutamic acid, aspartic acid and the like, salts with inorganic bases such as a sodium salt, a potassium salt and the like, and salts with organic bases such as N-methyl-D-glucamine, N,N'-dibenzyletylenediamine, 2-aminoethanol, tris (hydroxymethyl)aminomethane, arginine, lysine and the like.

In some methods of the invention where mizagliflozin is administered, the pharmaceutical salt is selected from mizagliflozin monosebacate and mizagliflozin hemifumarate dehydrate. Mizagliflozin hemifumarate dihydrate, from U.S. Pat. No. 8,354,382, is shown below:

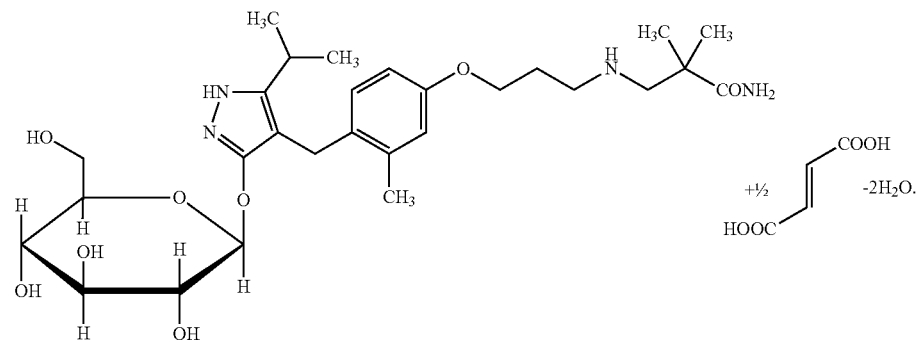

Mizagliflozin monosebacate, from U.S. Pat. No. 8,399,418, is shown below:

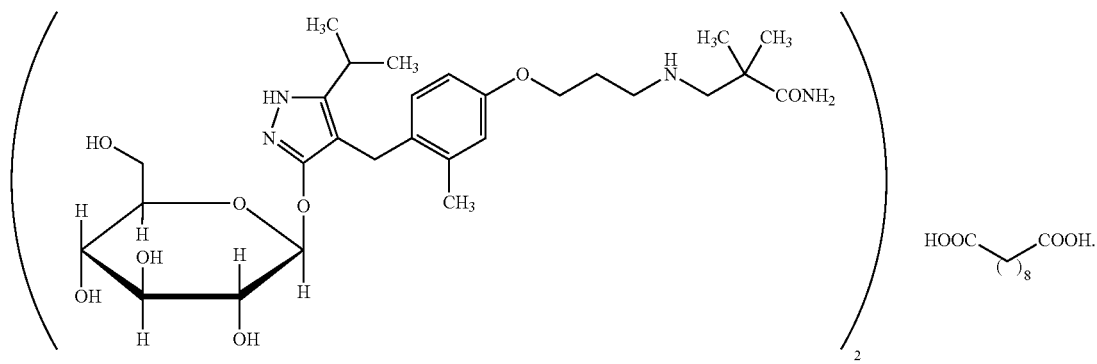

In a method of the invention, the SGLT inhibitor compound of Formula I or Formula II is administered at a dosage of from about 0.1 mg/day to about 160 mg/day. For example the dosage is 0.1 mg/day, 0.2 mg/day, 0.5 mg/day, 1 mg/day, 2 mg/day, 3 mg/day, 5 mg/day, 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, or 160 mg/day. Preferably, the dosage is from about 1 mg/day to about 60 mg/day. For example, the dosage is 1 mg/day, 2 mg/day, 3 mg/day, 4 mg/day, 5 mg/day, 6 mg/day, 7 mg/day, 8 mg/day, 9 mg/day, 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 24 mg/day, 27 mg/day, 30 mg/day, 33 mg/day, 36 mg/day, 39 mg/day, 42 mg/day, 45 mg/day, 48 mg/day, 51 mg/day, 54 mg/day, 57 mg/day, or 60 mg/day. In some methods of the invention the SGLT inhibitor compound of Formula I or Formula II is administered as a pharmaceutically acceptable salt thereof. In such methods, the daily dose refers to the mg/day of the compound. A therapeutically effective amount for administration is determined by a treating physician.

The daily dose can be divided into one or more, for example, two or three or four unit doses administered per day A unit dose is the amount of compound administered at one time. In a preferred method of the invention, SGLT inhibitor compound of Formula I or Formula II is administered at a unit dose of from about 0.1 mg to about 20 mg, three times a day. For example, the dosage is 0.1 mg, three times a day; 0.2 mg, three times a day; 0.5 mg, three times a day; 1 mg, three times a day; 2 mg, three times a day; 3 mg, three times a day; 4 mg, three times a day; 5 mg, three times a day; 6 mg, three times a day; 7 mg, three times a day; 8 mg, three times a day; 9 mg, three times a day; 10 mg, three times a day; 11 mg, three times a day; 12 mg, three times a day; 13 mg, three times a day; 14 mg, three times a day; 15 mg, three times a day; 16 mg, three times a day; 17 mg, three times a day; 18 mg, three times a day; 19 mg, three times a day; or 20 mg, three times a day. In some methods of the invention the SGLT inhibitor compound of Formula I or Formula II is administered as a pharmaceutically acceptable salt thereof. In such methods, the unit dose refers to the mg of the compound.

In a preferred method of the invention, the SGLT inhibitor compound of Formula I or Formula II, or pharmaceutically acceptable salt thereof, is administered before a meal. For example, the SGLT inhibitor compound of Formula I or Formula II, or pharmaceutically acceptable salt thereof, is administered once before breakfast, once before lunch, and once before dinner, daily.

In methods according to the invention pharmaceutical compositions of SGLT1 inhibitor compounds of Formula I or Formula II, or pharmaceutically acceptable salt thereof, are employed using various dosage forms depending on their uses. Examples of orally administered dosage forms include powders, granules, fine granules, dry syrups, tablets, tablet triturates, chewable lozenges, rapidly dissolving tablets, multiple compressed tablets, uncoated tablets, enteric coated tablets, capsules and the like. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Multiple compressed tablets are compressed tablets made by more than one compression cycle, including layered, press-coated, and dry-coated tablets. Tablets may also be coated using microencapsulation to delay disintegration and absorption in the gastrointestinal tract and thereby provide a sustained action over a longer period. The pharmaceutical compositions of SGLT1 inhibitor compounds of Formula I or Formula II also include sustained release formulation including gastrointestinal mucoadhesive formulation (e.g., International publications Nos. WO99/10010, WO99/26606, and Japanese patent publication No. 2001-2567).

The pharmaceutical compositions can be prepared by admixing with or by diluting and dissolving with an appropriate pharmaceutical additive such as excipients, disintegrators, binders, fillers, lubricants, diluents, buffers, isotonicities, antiseptics, moistening agents, emulsifiers, dispersing agents, stabilizing agents, dissolving aids and the like, and formulating the mixture in accordance with conventional methods. In case of the uses of the compound of SGLT1 inhibitor compounds of Formula I or Formula II in combination with the drug(s) other than SGLT1 inhibitors, they can be prepared by formulating each active ingredient together or individually.

In some methods of the invention, the SGLT1 inhibitor compound of Formula I or Formula II, or pharmaceutically acceptable salt thereof, is administered in combination with at least one alpha-glucosidase inhibitor or glucagon-like peptide (GLP)-1 receptor antagonist. The alpha-glucoside inhibitor is preferably selected from the group consisting of acarbose, voglibose, and miglitol. Preferably, the GLP-1 receptor antagonist is the peptide fragment of Exenatide, exendin 9-39. In the methods of the invention where the SGLT1 inhibitor compound of Formula I or Formula II, or pharmaceutically acceptable salt thereof, is administered in combination with such drugs, the dosage of the SGLT1 inhibitor compound of Formula I or Formula II can be decreased, depending on the dosage of the alpha-glucosidase inhibitor or GLP-1 receptor antagonist.

EXAMPLES

Example 1

Selective inhibition study. Inhibition constants (Ki) of mizagliflozin for rat and human SGLT1 and SGLT2 were determined measuring concentration-dependent effects of test compound on uptake of radiolabeled methyl-$\alpha$-D-glucopyranoside ($\alpha$-MG) into COS-7 cells transiently transfected with cloned SGLT1 or SGLT2. Mizagliflozin was assessed at concentrations from 1 to 30 μM and 3 to 100 μM for human and rat SGLT2, respectively. It was assessed at concentrations from 30 nM to 1 μM and 10 to 30 nM for human and rat SGLT1, respectively. $\alpha$-MG test concentrations were 0.3 and 1 mM. Data were analyzed and Ki determined using Dixon plots of initial transport rates. The in vitro inhibition constants of mizagliflozin for rat SGLT1 and rat SGLT2 were determined and a positive control for both SGLT1 and SGLT2, phlorizin, was included for comparison. The mizagliflozin Ki for rat SGLT1 was 31.2 nM, indicating good selectivity when compared to the mizagliflozin Ki for rat SGLT2 of 14000 nM. The inhibition constants for phlorizin were 135 and 41.1 nM for SGLT1 and SGLT2, respectively. Inhibition constants were also determined for human SGLT1 and SGLT2. See FIG. 10 and FIG. 11. The mizagliflozin inhibition constants for human SGLT1 and human SLGT2 were 27.0 nM and 8170 nM, respectively. Thus, mizagliflozin had potent inhibitory effect on human SGLT1 and high selectivity for SGLT1 compared to SGLT2. Intersection patterns on Dixon plots of transport inhibition rates indicate that inhibition of SGLT1 is competitive with substrate for both species.

Example 2

Study on normal rats. The efficacy of mizagliflozin (decreasing plasma glucose levels) in normal Sprague Dawley rats was determined in a mixed carbohydrate tolerance test. Normal rats were fasted for 16 hours and then given an oral loading dose of 2.0 g/kg of mixed carbohydrate (soluble starch:sucrose:lactose monohydrate=6:3:1). Mizagliflozin (KGA-3235 sebacate), or water as the vehicle control, was then administered as a single oral dose to groups of male rats (n=8/group) at doses of 0.03, 0.1, 0.3, and 1 mg/kg. Voglibose, a glucosidase inhibitor similar to acarbose, was used as a positive control and was administered as a single oral dose to male rats (n=8/group) at dose levels of 0.1, 0.3 and 1 mg/kg. Blood samples were collected just prior to loading with mixed carbohydrate and at 0.5, 1, 2, 3, 4, and 6 hours after loading. Plasma glucose concentrations were determined and $\Delta AUC0$-1 h (the change in AUC) for plasma glucose was calculated.

Figure 1B:
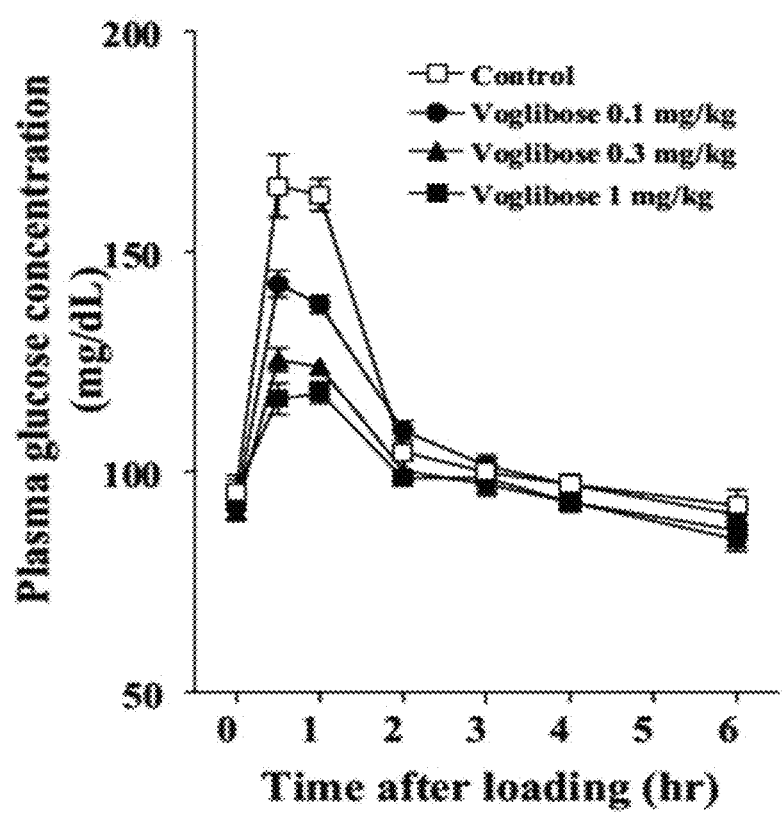
Figure 2:
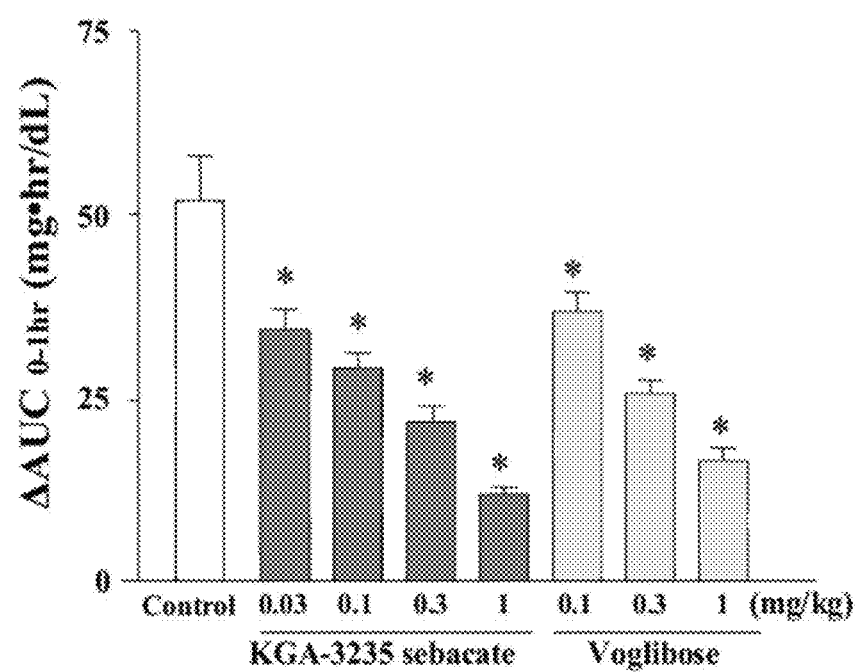
FIG. 2 shows effects of mizagliflozin, referred to as KGA-3235 sebacate, and voglibose on ΔAUC0-1 hr in normal rats following oral mixed carbohydrate load.
Figure 3:
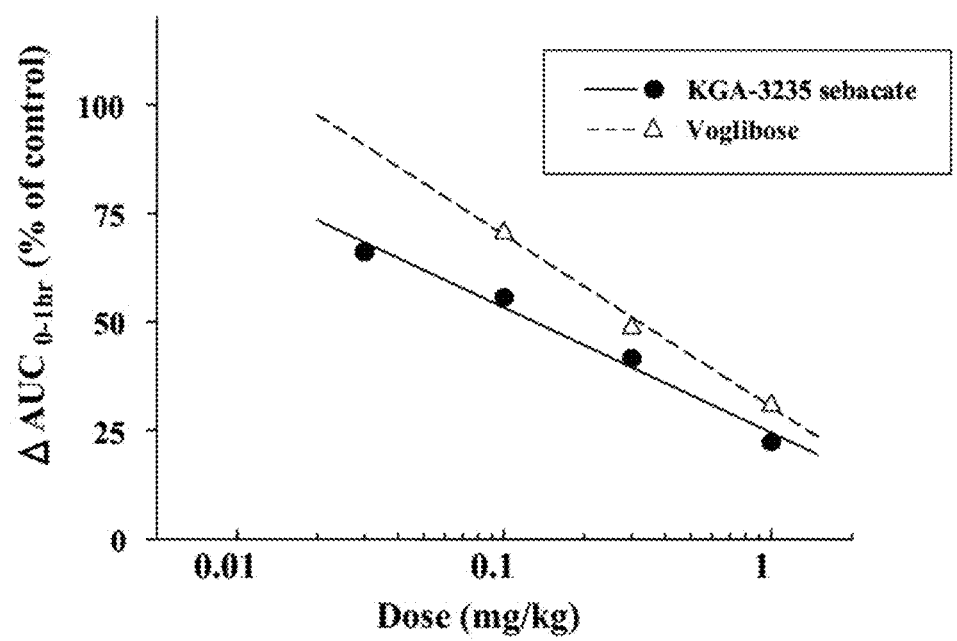
FIG. 3 shows effects of mizagliflozin, referred to as KGA-3235 sebacate, and voglibose on mean ΔAUC0-1 hr (% of control) in normal rats following oral mixed carbohydrate load.

Mizagliflozin reduced plasma glucose concentrations (FIG. 1) and significantly lowered the $\Delta AUC0$-1 h after loading of mixed carbohydrate when compared to the vehicle control (FIG. 2). A significant decrease in $\Delta AUC0$-1 h was also seen after administration of voglibose. The 50% effective dose (ED50) calculated from the mean $\Delta AUC0$-1 h (% of control) for all dose levels of mizagliflozin was 0.130 mg/kg of mizagliflozin. The ED50 for voglibose was 0.320 mg/kg (FIG. 3).

Example 3

Study in diabetic rats. Mizagliflozin was tested in a rat model for diabetes and efficacy, as measured by a relative decrease in plasma glucose, was determined using a mixed carbohydrate tolerance test. Diabetic model rats were prepared by intravenous administration of streptozotocin (STZ) to induce diabetes. Seven days after STZ administration, rats were fasted for 16 hours and then given an oral loading dose of 2.0 g/kg of mixed carbohydrate (soluble starch:sucrose:lactose monohydrate=6:3:1). Mizagliflozin, or water as the vehicle control, was then administered as a single oral dose to groups of male rats (n=8/group) at doses of 0.01, 0.03, 0.1, and 0.3 mg/kg. Another control group was given vehicle and consisted of normal male Sprague Dawley rats that were not administered STZ. Voglibose was also administered as a single oral dose to male rats (n=8/group) at dose levels of 0.03, 0.1 and 0.3 mg/kg. Blood samples were collected just prior to loading with mixed carbohydrate and at 0.5, 1, 2, 3, 4, and 6 hours after loading. Plasma glucose concentrations were determined and $\Delta AUC0$-1 h for plasma glucose was calculated.

Figure 4A:
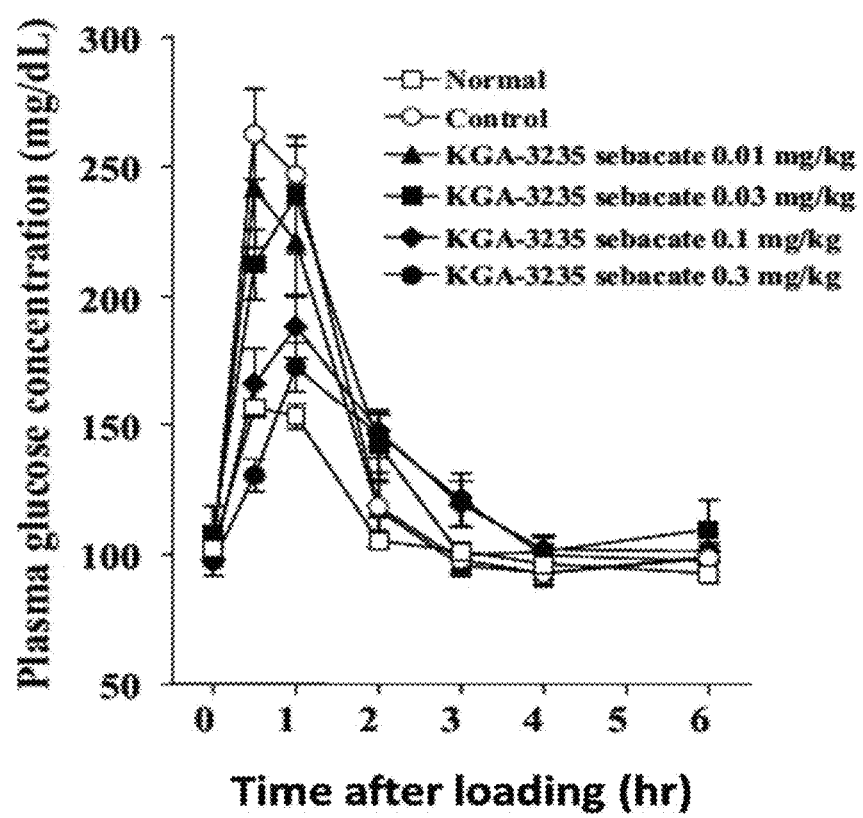
FIG. 4(A-B) shows effects of mizagliflozin, referred to as KGA-3235 sebacate, and voglibose on oral glucose excursion in STZ-induced diabetic rats following oral mixed carbohydrate load.
Figure 4B:
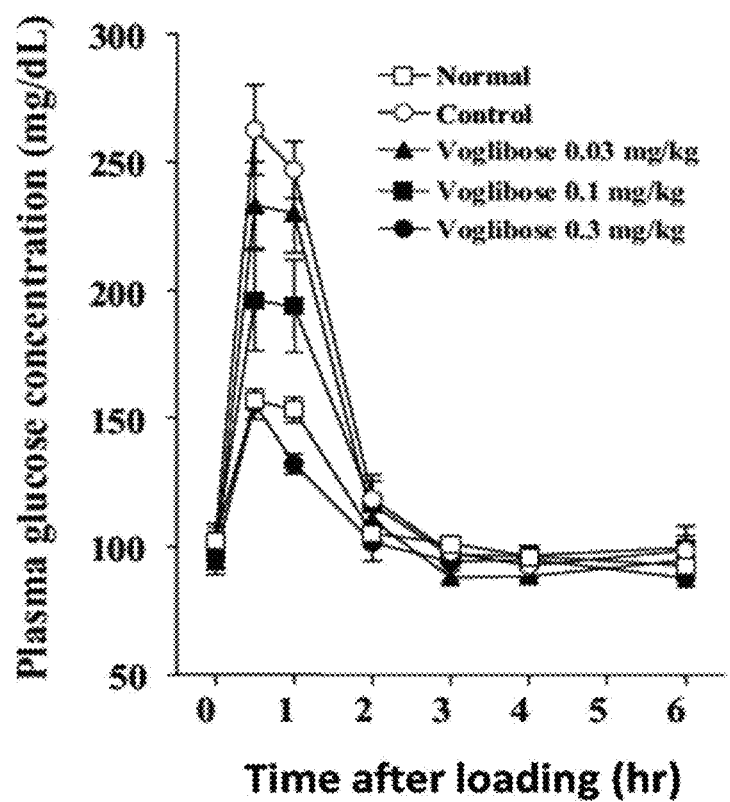
Figure 5:
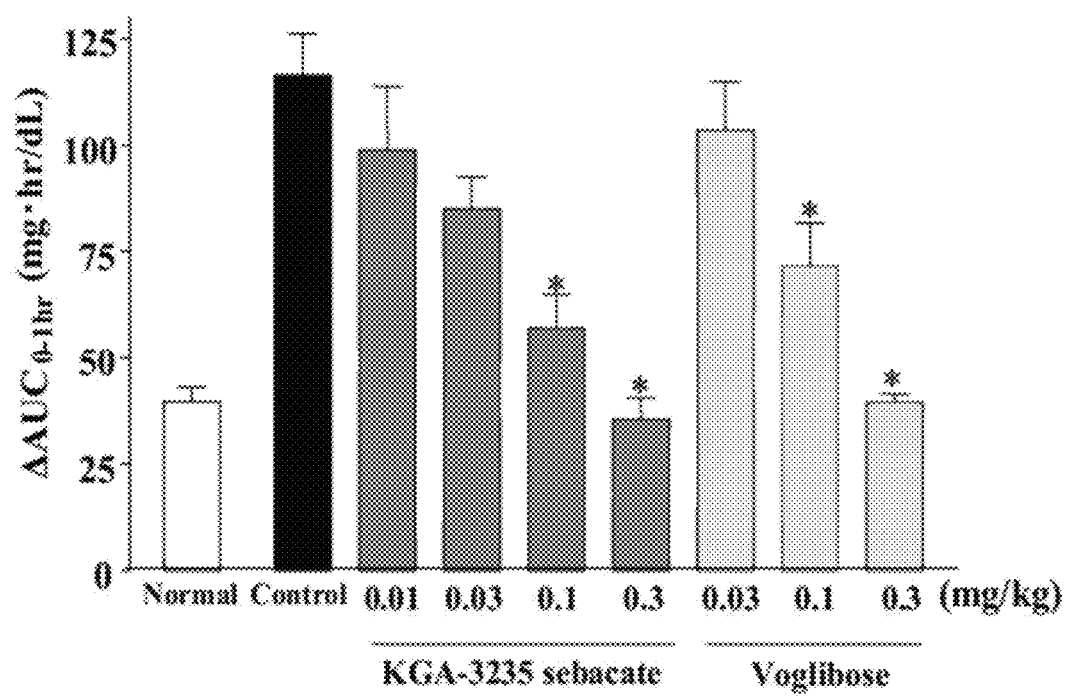
FIG. 5 shows effects of mizagliflozin, referred to as KGA-3235 sebacate, and voglibose on the ΔAUC0-1 hr in STZ-induced diabetic rats following oral mixed carbohydrate load.

Mizagliflozin reduced plasma glucose concentrations (FIG. 4) and significantly lowered the $\Delta AUC0$-1 h in STZ-induced diabetic rats after loading of mixed carbohydrate when compared to the vehicle control (FIG. 5). A significant decrease in $\Delta AUC0$-1 h was also seen after administration of voglibose. The ED50 calculated from the mean $\Delta AUC0$-1 h (% of control) for all dose levels of mizagliflozin was 0.096 mg/kg of mizagliflozin.

Example 4

Study in diabetic rats using oral glucose tolerance test. Efficacy of mizagliflozin was tested in a rat model for diabetes using an oral glucose tolerance test (OGTT). Diabetic model rats were prepared by intravenous administration of STZ to induce diabetes. Seven days after STZ administration, rats were fasted for 16 hours and then given an oral loading dose of 2.0 g/kg of glucose. Mizagliflozin, or water as the vehicle control, was then administered as a single oral dose to groups of male rats (n=8/group) at doses of 0.03, 0.1, 0.3, and 1 mg/kg. Another control group was given vehicle and consisted of normal male Sprague Dawley rats that were not administrated STZ. Voglibose was also administered as a single oral dose to male rats (n=8/group) at dose levels of 0.1, 0.3 and 1 mg/kg. Blood samples were collected just prior to loading with mixed carbohydrate and at 0.5, 1, 2, 3, 4, and 6 hours after loading. Plasma glucose concentrations were determined and $\Delta AUC0$-1 h for plasma glucose was calculated.

Figure 6A:
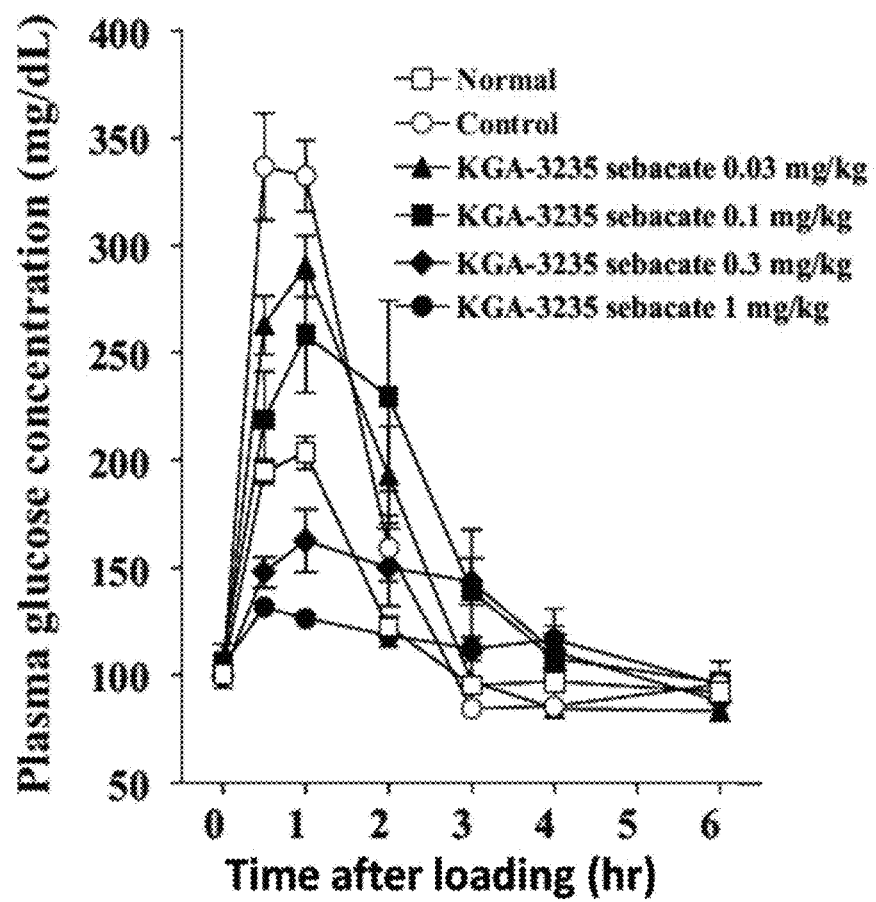
FIG. 6A-B shows effects of mizagliflozin, referred to as KGA-3235 sebacate, and voglibose on oral glucose excursion in STZ-induced diabetic rats following OGTT.
Figure 6B:
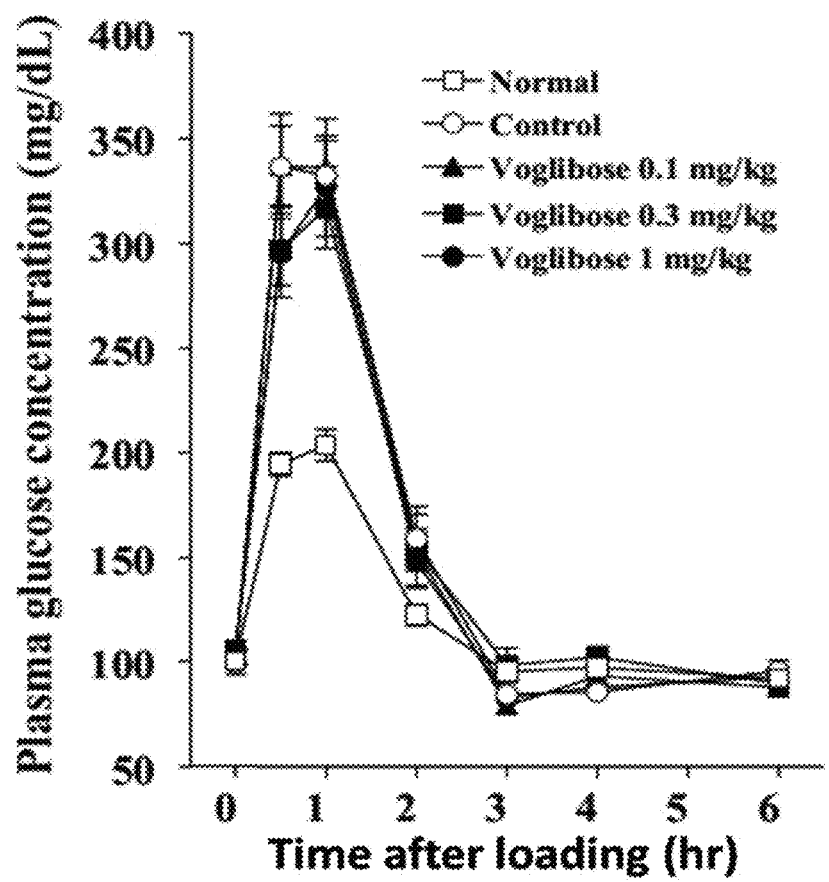
Figure 7:
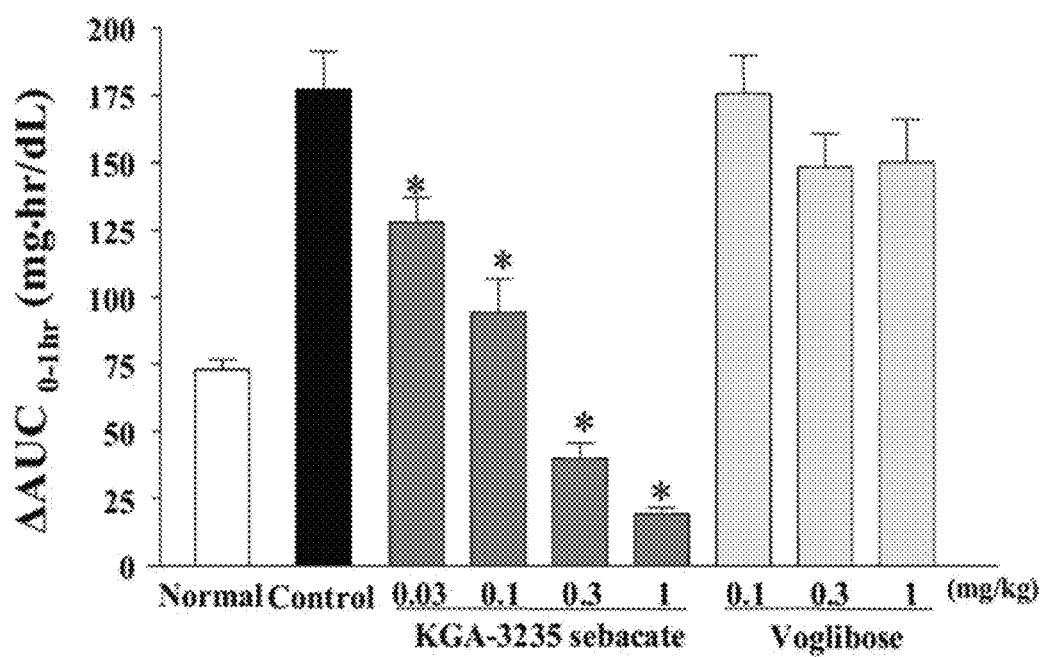
FIG. 7 shows effects of mizagliflozin, referred to as KGA-3235 sebacate, and voglibose on the ΔAUC0-1 hr in STZ-induced diabetic rats following OGTT.

Mizagliflozin reduced plasma glucose concentrations (FIG. 6) and significantly lowered the $\Delta AUC0$-1 h after loading of glucose when compared to the vehicle control (FIG. 7). A significant decrease in $\Delta AUC0$-1 h was also seen after administration of voglibose. The ED50 calculated from the mean $\Delta AUC0$-1 h (% of control) for all dose levels of mizagliflozin was 0.099 mg/kg of mizagliflozin.

Figure 8:
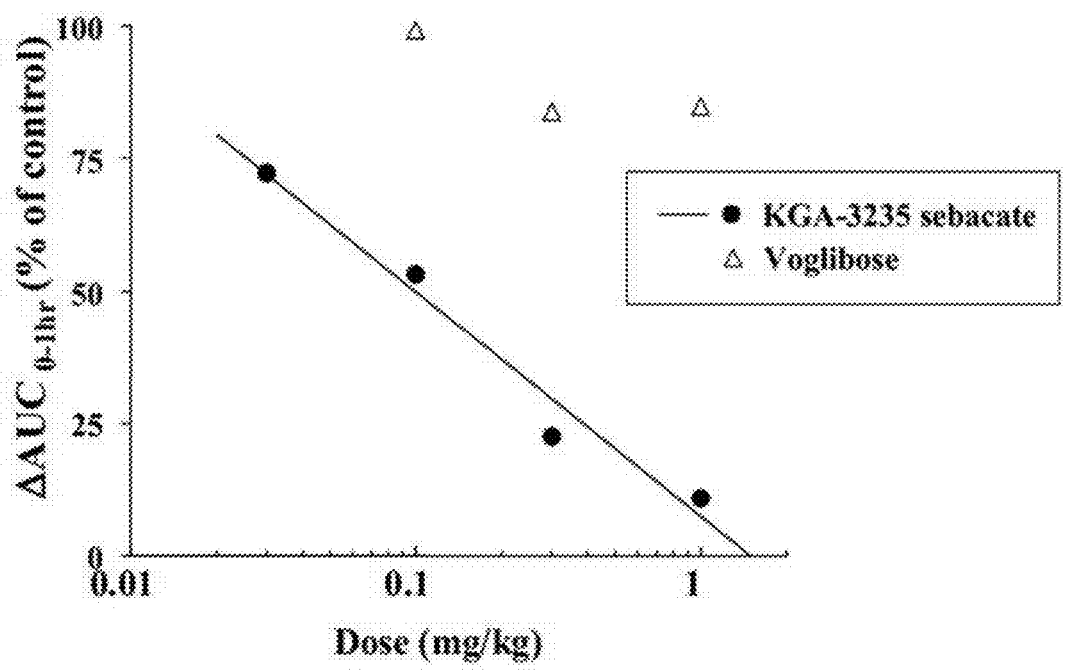
FIG. 8 shows dose-response relationships for mean ΔAUC0-1 hr (% of control) in response to mizagliflozin, referred to as KGA-3235 sebacate, and voglibose after OGTT in STZ-induced diabetic rats.

The dose-response relationships for mean $\Delta AUC0$-1 h (% of control) in response to mizagliflozin and voglibose are shown in FIG. 8. The 50% effective dose (ED50) calculated from mean ΔAUC0-1 h (% of control) was 0.099 mg/kg (as KGA-3235) in the case of mizagliflozin. Even ΔAUC0-1 h in the group administrated maximum dose, 1 mg/kg of voglibose was not half or less than half that in the control group, and so ED50 of voglibose was not calculated.

Example 5

Figure 9:
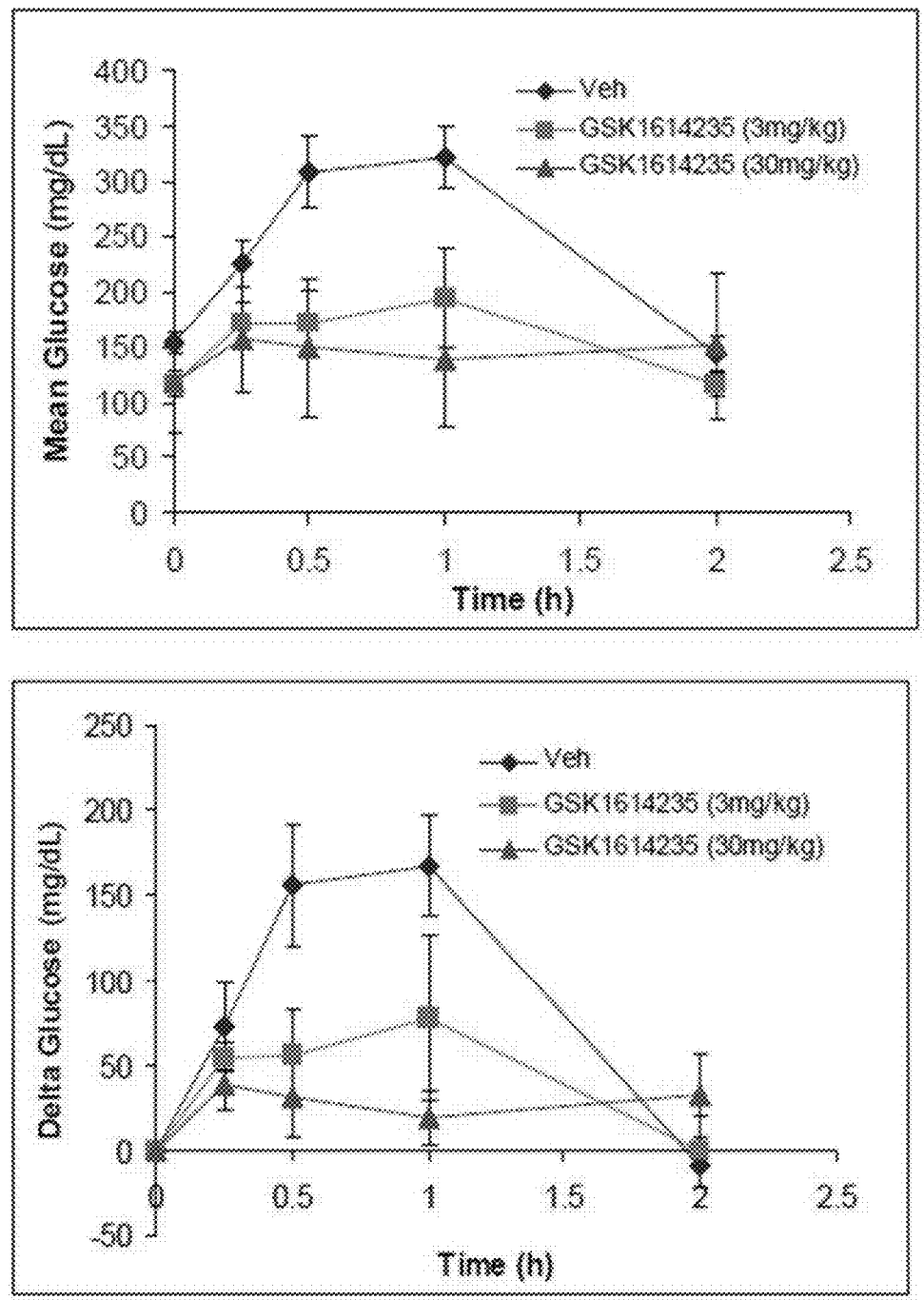
FIG. 9 shows effects of 3 mg/Kg and 30 mg/Kg doses of mizagliflozin, referred to as GSK1614235, on oral glucose excursions in DIO marmosets.
Figure 10A:
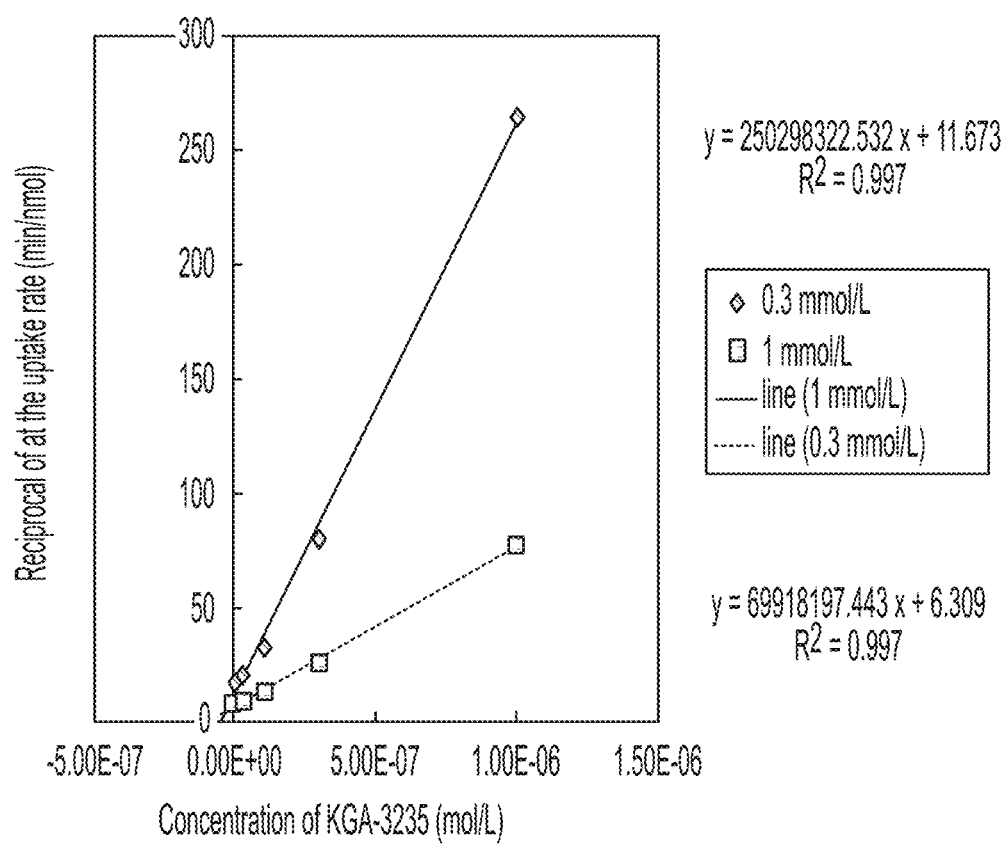
FIG. 10 (A-D) shows the Dixon plots to calculate the inhibition constant of mizagliflozin (KGA-3235) for human SGLT1.
Figure 10B:
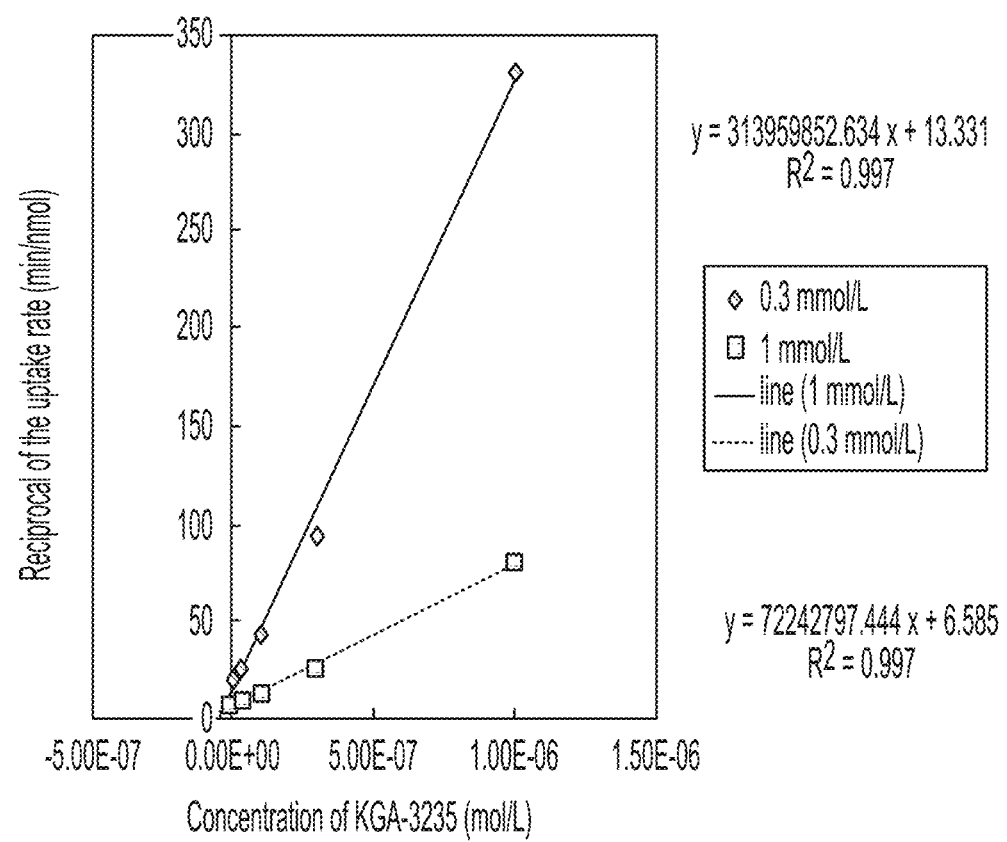
Figure 10C:
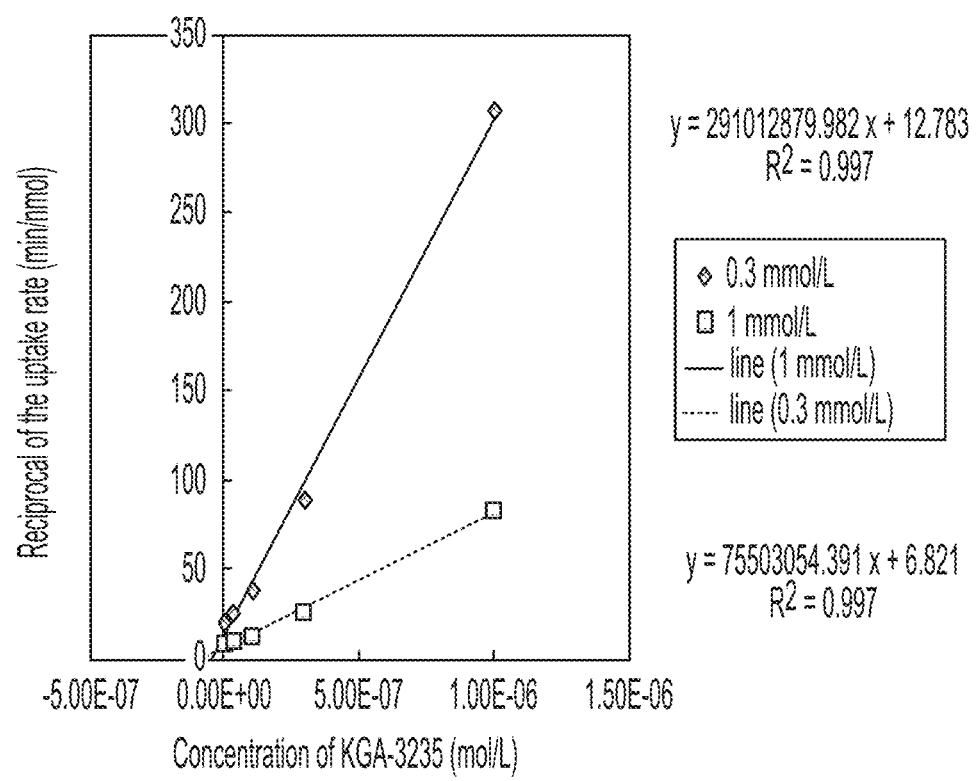
Figure 10D:
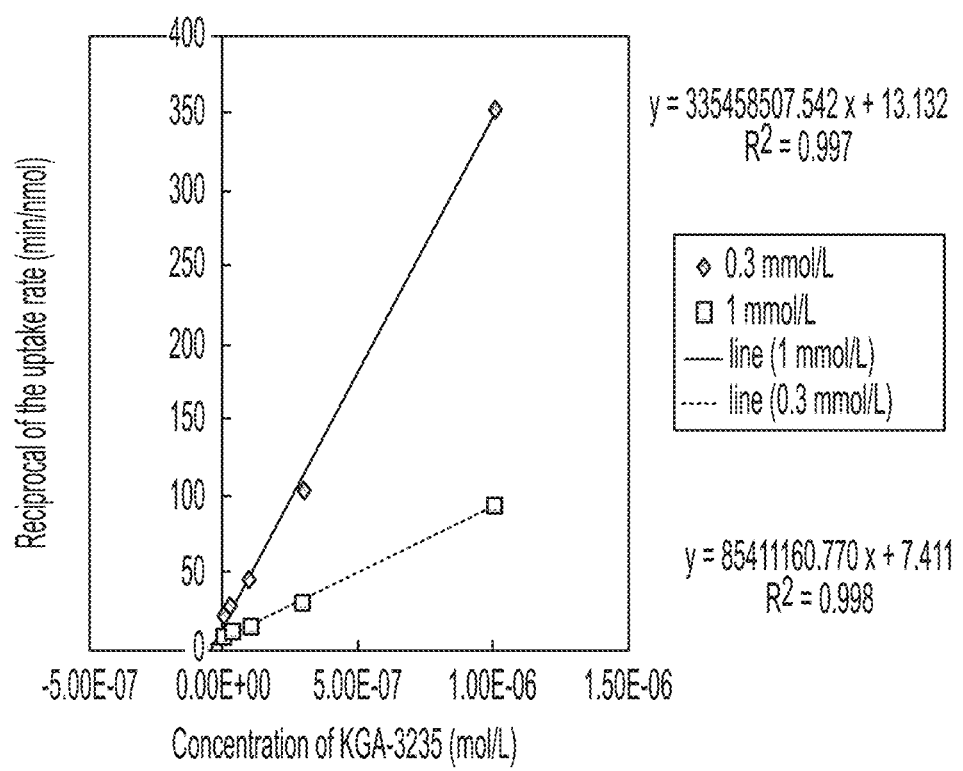
Figure 11A:
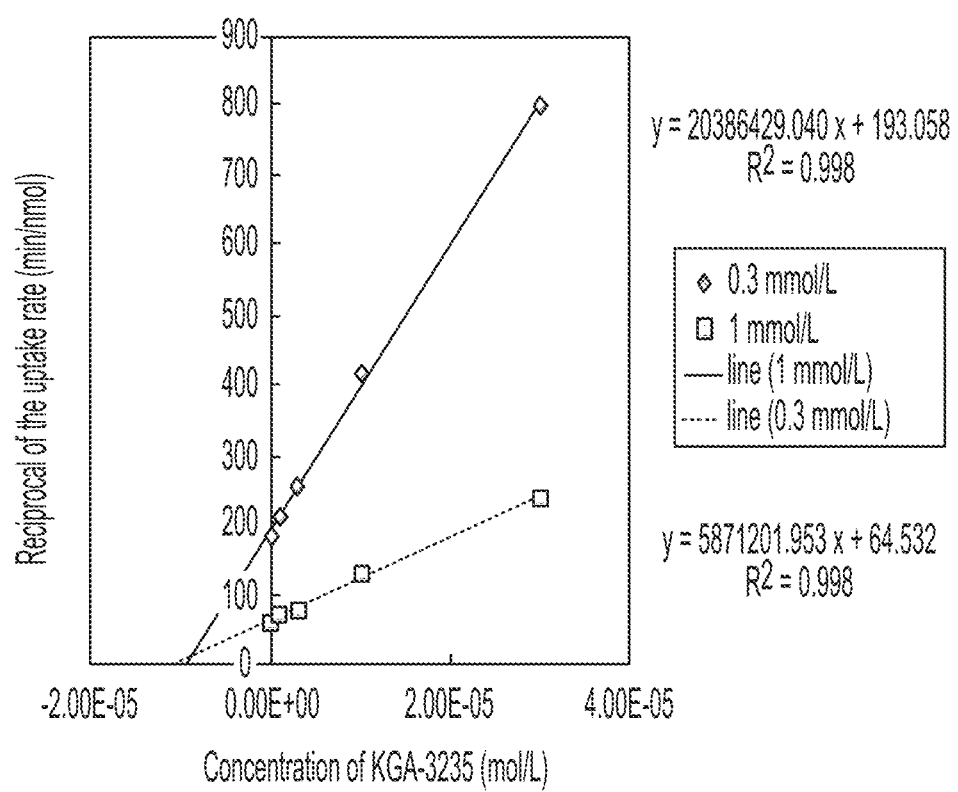
FIG. 11(A-D) shows the Dixon plots to calculate the inhibition constant of mizagliflozin, referred to as KGA-3235, for human SGLT2.
Figure 11B:
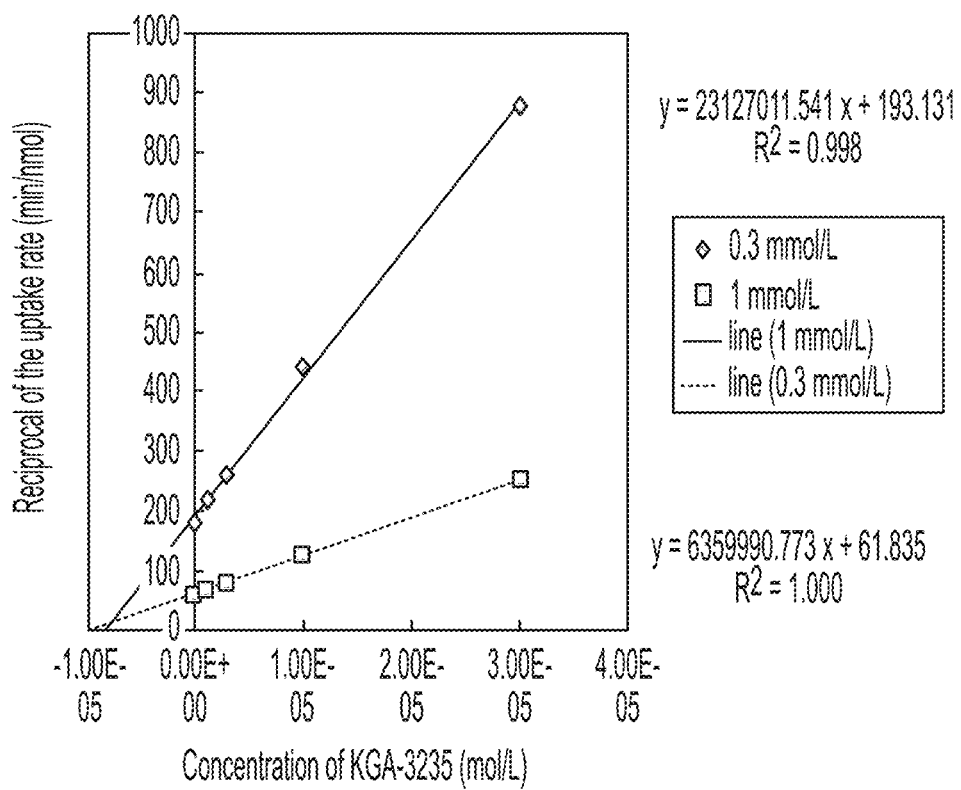
Figure 11C:
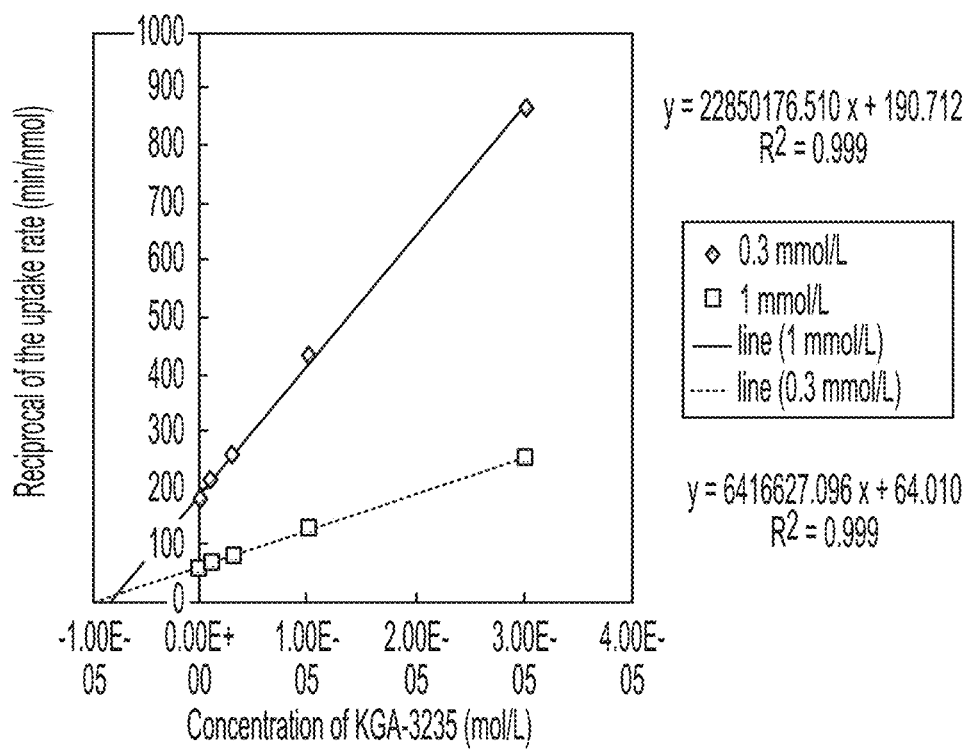
Figure 11D:
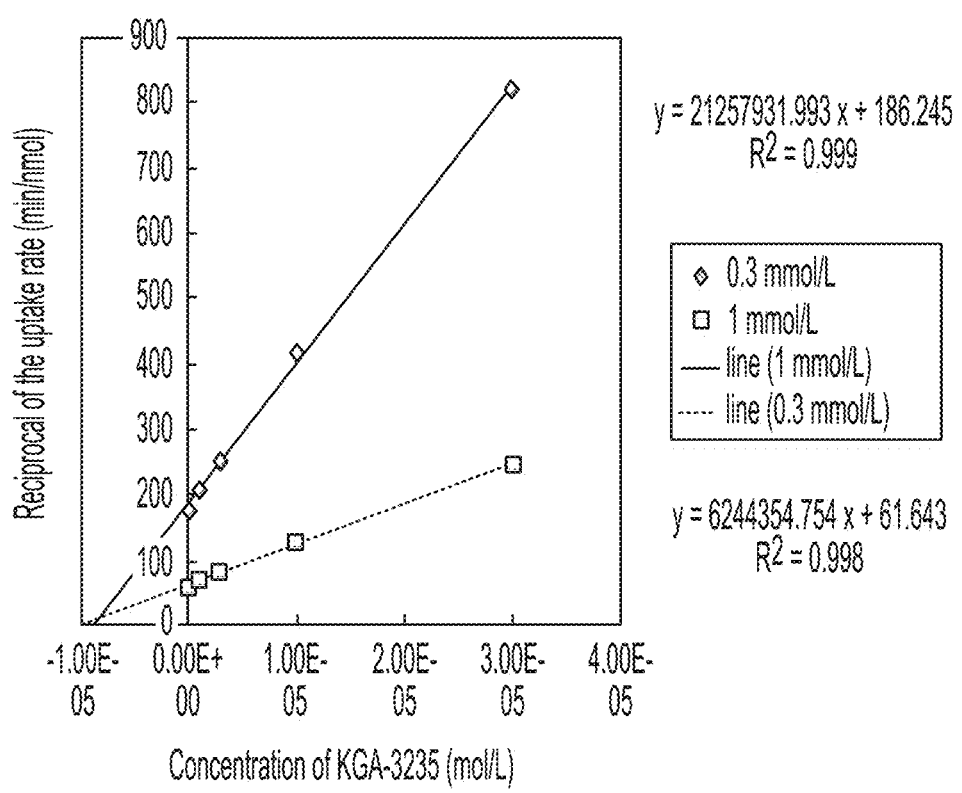

Study on plasma glucose levels in marmosets. Mizagliflozin was evaluated in the Diet-induced obese (DIO) marmoset, a polygenic non-human primate model of obesity. Rimonabant, a canabinoid receptor (CB-1) antagonist that was marketed by Sanofi-Aventis for weight loss in obese patients, was administered at a maximal effective dose of 20 mg/kg twice daily as a positive control. Mizagliflozin was administered orally twice daily to DIO male marmosets (n=8/group) for 2 weeks at BID doses of 3 and 30 mg/kg/day (or only vehicle, aqueous hydroxypropylmethyl-cellulose 0.1%). Effects on body weight and body composition, and serum chemistry parameters were measured and glucose excursions during post-treatment OGTTs were also determined after administration of an oral loading dose of glucose (2.0 g/kg). Doses of 3 and 30 mg/kg mizagliflozin had no significant effects on either body weight or body composition (fat or lean mass) or any serum chemistry parameters measured. Two weeks dosing with mizagliflozin resulted in a blunting of the glucose excursions during post-treatment OGTT's (FIG. 9). No signs of diarrhea were observed at any time during the study.

Example 6

Single dose study in humans. A single oral dose of 2 mg, 5 mg, 10 mg, 20 mg, 40 mg, 80 mg, and 160 mg of mizagliflozin were administered to healthy adult male volunteers by a placebo-controlled, randomized, double-blind method. The single dose was administered orally immediately before breakfast with approximately 200 mL of water after fasting for at least 10 hours. Pharmacodynamic effect parameters (blood glucose level, insulin, GLP-1, and gastric inhibitory polypeptide (GIP)) were measured. Concentrations at each time point were measured, and summary statistics and coefficient variation (CV) were calculated for $AUC_{0-t}$; t was up to 6 hours postdose. The time points were: before administration and 0.5, 1, 1.5, 2, 3, 4, 5, and 6 hours after administration. Blood glucose level and insulin were measured to evaluate in an exploratory manner the inhibitory effect on postprandial hyperglycemia. GLP-1 and GIP were measured to evaluate in an exploratory manner the incretin secretory action.

Postprandial blood glucose level and blood insulin concentration were suppressed with an increase in the dose of mizagliflozin, and the time for each to reach the peak value tended to be delayed. As shown in Table 1, elevation in glucose was suppressed in all mizagliflozin groups and AUC tended to decrease in general. Inhibitory effect on hyperglycemia was prominent up to 1 h after eating. The time to reach max blood glucose tended to be delayed with increasing dose. As shown in Table 2, postprandial elevation in insulin was suppressed with an increase in mizagliflozin dose and time to reach peak value tended to be delayed. AUC for insulin tended to decrease in general with an increase mizagliflozin dose. As for the effect of mizagliflozin administration on the secretory action of incretin, suppression of GIP secretion was suggested (Table 4). AUC for GIP was lower in each mizagliflozin group indicating the elevation was suppressed. GIP concentrations peaked more than 3 h after treatment. No clear conclusion could be reached regarding the effect on GLP-1 (Table 3). GLP-1 was higher in all mizagliflozin treatment groups but change in GLP-1 could not be evaluated due to variation in mean baseline level between subjects was large (1.9 to 9.9 pmol*h/L).

TABLE 1

| | Glucose | | |
| --- | --- | --- | --- |
| Treatment | Glucose (mg/dL) | Time (h) to peak | AUC 0-6 glucose (mg*h/dL) |
| PBO | 162 | 0.5 | 660.5 |
| 2 mg | 128.7 | 1.5 | 628.3 |
| 5 mg | 130.3 | 1 | 631.3 |
| 10 mg | 143.8 | 1.5 | 661.9 |
| 20 mg | 113.7 | 2 | 612.9 |
| 40 mg | 130.3 | 1.5 | 629.1 |
| 80 mg | 116 | 3 | 611.92 |
| 160 mg | 106.5 | 3 | 606.2 |

TABLE 2

| | Insulin | | |
| --- | --- | --- | --- |
| Treatment | Insulin (uU/ml) | Time (h) to peak | AUC 0-6 Insulin (uU*h/ml) |
| PBO | 64.6 | 0.5 | 144.1 |
| 2 mg | 40.38 | 1.5 | 123.2 |
| 5 mg | 47.1 | 1.5 | 140.7 |
| 10 mg | 39 | 2 | 120.4 |
| 20 mg | 25.9 | 3 | 89.7 |
| 40 mg | 33.8 | 1.5 | 99.7 |
| 80 mg | 20.5 | 3 | 70.9 |
| 160 mg | 16.2 | 3 | 62.7 |

TABLE 3

| | GLP-1 (active) | | |
| --- | --- | --- | --- |
| Treatment | GLP-1 (pmol/L) | Time (h) to peak | AUC 0-6 GLP-1 (pmol*h/L) |
| PBO | 5.5 | 0.5 | 23.6 |
| 2 mg | 6.4 | 0.5 | 23.7 |
| 5 mg | 6.1 | 0.5 | 28.5 |
| 10 mg | 8.7 | 0.5 | 41.5 |
| 20 mg | 11.6 | 1.5 | 55.8 |
| 40 mg | 7.5 | 0.5 | 32.6 |
| 80 mg | 5.5 | 2 | 24.1 |
| 160 mg | 7.9 | 2 | 39.5 |

TABLE 4

| | GIP | | |
| --- | --- | --- | --- |
| Treatment | GIP (pg/ml) | Time (h) to peak | AUC 0-6 GIP (pg*h/ml) |
| PBO | 247.7 | 2 | 1064 |
| 2 mg | 183.6 | 4 | 818.5 |
| 5 mg | 194.5 | 3 | 856.9 |
| 10 mg | 252.3 | 4 | 945.7 |
| 20 mg | 216.7 | 4 | 783.9 |
| 40 mg | 166.7 | 4 | 591.4 |
| 80 mg | 161.6 | 5 | 621.5 |
| 160 mg | 117.9 | 5 | 445.5 |

Example 7

Repeat dose study in humans. Oral doses of 2 mg, 5 mg, 10 mg, 20 mg, of mizagliflozin, placebo or miglitol 50 mg per dose three times daily to healthy adult male volunteers by a randomized, placebo-controlled, parallel-group, double-blind comparison method. The dose was orally administered with approximately 150 mL of water once daily immediately before breakfast on Days 1 and 13, and three times daily immediately before every meal on Days 3 to 12.

Changes in the following parameters and $\Delta AUC$ from 0 to t* hours after breakfast, lunch, and evening meal were measured: Blood glucose level, Serum insulin concentration, Blood active GLP-1 concentration, and Blood total GIP concentration, where t=0.5, 1, 1.5, 2, and 3 (t=0.5, 1, 1.5, 2, 3, and 5 only after breakfast).

In the miglitol group, hyperglycemia was suppressed after breakfast, lunch, and evening meal, as compared to the placebo group. In addition, inhibition of insulin secretion along with inhibition of hyperglycemia, an increase in total GLP-1 concentration, a tendency toward increase in active GLP-1 concentration, and inhibition of increase in total GIP concentration were seen. In the mizagliflozin group, hyperglycemia was suppressed after breakfast, lunch, and evening meal on a level equivalent to the miglitol group. In the mizagliflozin group, inhibition of insulin secretion along with inhibition of hyperglycemia was seen the same as in the miglitol group. In the mizagliflozin group, increase in total GLP-1 concentration was seen on a level equivalent to the miglitol group. In the mizagliflozin group, a tendency toward increase in active GLP-1 concentration was seen as in the case of the miglitol group. In the mizagliflozin group, increase in total GIP concentration was seen on a level equivalent to the miglitol group. These pharmacodynamic effects more or less persisted during 10-day repeated administration. There was no correlation between plasma mizagliflozin concentration and the pharmacodynamic effects. Measurements in Tables 5-8 were performed on Day 3 after breakfast.

TABLE 5

| | Glucose | | |
|---|---|---|---|
| Treatment | Glucose (mg/dL) | Time (h) to peak | AUC 0-5 glucose (mg*h/dL) |
| PBO | 166.9 | 0.5 | 569.2 |
| 2 mg | 131.6 | 1 | 550.6 |
| 5 mg | 118.6 | 1.5 | 524.6 |
| 10 mg | 121.3 | 1.5 | 541.3 |
| 20 mg | 121 | 1.5 | 522.4 |
| Miglitol 50 mg | 121.6 | 1.5 | 543.7 |

TABLE 6

| | Insulin | | |
|---|---|---|---|
| Treatment | Insulin (uU/ml) | Time (h) to peak | AUC 0-5 Insulin (uU*h/ml) |
| PBO | 121.15 | 0.5 | 246.76 |
| 2 mg | 58.05 | 1.5 | 166.61 |
| 5 mg | 44 | 2 | 146.08 |
| 10 mg | 55.13 | 1 | 176.7 |
| 20 mg | 47.69 | 1.5 | 142.25 |
| Miglitol 50 mg | 40.4 | 2 | 138.33 |

TABLE 7

| | GLP-1 (active) | | |
|---|---|---|---|
| Treatment | GLP-1 (pmol/L) | Time (h) to peak | AUC 0-5 GLP-1 (pmol*h/L) |
| PBO | 4.79 | 0.5 | 17.76 |
| 2 mg | 5.98 | 0.5 | 21.21 |
| 5 mg | 5.95 | 0.5 | 22.36 |
| 10 mg | 10.01 | 0.5 | 41.12 |
| 20 mg | 6.01 | 0.5 | 24.74 |
| Miglitol 50 mg | 6.21 | 0.5 | 20.5 |

TABLE 8

| | GIP | | |
|---|---|---|---|
| Treatment | GIP (pg/ml) | Time (h) to peak | AUC 0-5 GIP (pg*h/ml) |
| PBO | 335.25 | 2 | 1310.98 |
| 2 mg | 285 | 3 | 1096.21 |
| 5 mg | 280.88 | 3 | 1057.89 |
| 10 mg | 240.75 | 3 | 839.7 |
| 20 mg | 217.15 | 3 | 755.01 |
| Miglitol 50 mg | 235 | 3 | 897.03 |

Example 8

Figure 12:
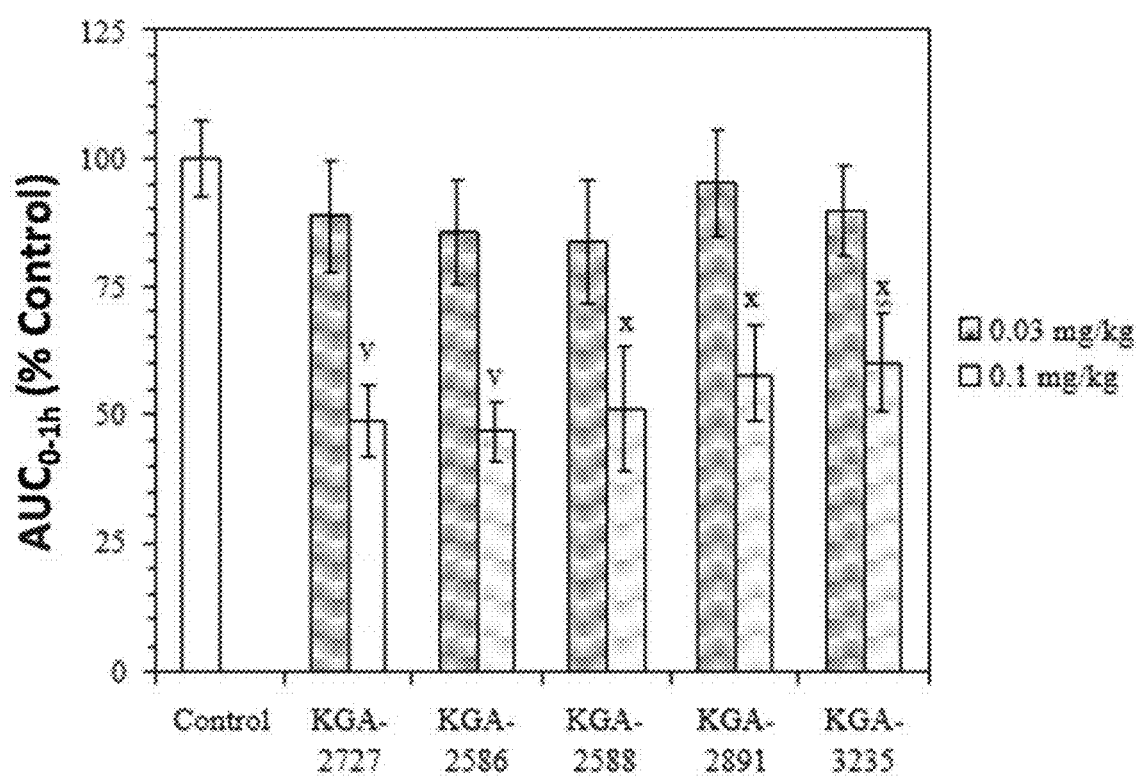
FIG. 12 shows the effects of SGLT1 inhibitors KGA-2727, KGA-2586, KGA-2588, KGA-2891 and KGA-3235 on $\Delta AUC_{(0-1\ h)}$ calculated from plasma glucose concentration after oral glucose administration (2 g/kg) in STZ-induced diabetic rats. Data represent the mean±S.E.M. Difference from STZ-control: x, P<0.05; y, P<0.01; z, P<0.001.

Study in diabetic rats with glucose. Diabetic rats, induced by intravenous injection of streptozotocin (STZ; 40 mg/kg), were used to determining plasma glucose concentration (PG) 1 hr after oral glucose tolerance test (OGTT). Rats fasted overnight were administered the test substance solution (KGA-2727, KGA-2586, KGA-2588, KGA-2891 or KGA-3235, 0.03 and 0.1 mg/kg) or the vehicle (distilled water) orally at a dosing volume of 5 mL/kg, and were then immediately administered 400 g/L glucose solution orally at a dosing volume of 5 mL/kg (2 g/kg). Blood was collected via the caudal artery immediately before dosing and 0.5, 1, 2, and 3 hr after dosing. The glucose concentration measurement in plasma used Glucose CII-Test Wako kit (Wako Pure Chemicals Industries, Ltd., Osaka, Japan). The variables used for efficacy assessment were the measurement values of the plasma glucose concentration and the area under the curve for plasma glucose concentration through 1 hr after loading ($\Delta AUC$0-1 hr). The $\Delta AUC_{0-1\ hr}$ for plasma glucose was calculated based on the trapezoid method using the change of plasma glucose concentrations from pre-value (0 hr). KGA-2727, KGA-2586, KGA-2588, KGA-2891 and KGA-3235 inhibited PG elevation after glucose administration dose dependently (Table 9 and FIG. 12).

TABLE 9

| | Control | KGA-2727 | | KGA-2586 | | KGA-2588 | | KGA-2891 | | KGA-3235 | |
|---|---|---|---|---|---|---|---|---|---|---|---|
| | | 0.03 mg/kg | 0.1 mg/kg | 0.03 mg/kg | 0.1 mg/kg | 0.03 mg/kg | 0.1 mg/kg | 0.03 mg/kg | 0.1 mg/kg | 0.03 mg/kg | 0.1 mg/kg |
| Body weight (g) | 292 ± 7 | 284 ± 6 | 286 ± 6 | 274 ± 4 | 282 ± 5 | 278 ± 3 | 290 ± 7 | 274 ± 5 | 281 ± 3 | 288 ± 7 | 273 ± 12 |
| Plasma glucose (mg/dL) | | | | | | | | | | | |
| 0 hr | 121 ± 5 | 120 ± 9 | 116 ± 6 | 128 ± 4 | 121 ± 8 | 137 ± 6 | 128 ± 8 | 124 ± 11 | 131 ± 5 | 128 ± 10 | 120 ± 12 |
| 0.5 hr | 395 ± 24 | 354 ± 34 | 233 ± 15$^y$ | 351 ± 22 | 236 ± 18$^z$ | 351 ± 29 | 249 ± 32$^y$ | 384 ± 36 | 277 ± 23$^x$ | 356 ± 25 | 262 ± 27$^y$ |
| 1 hr | 351 ± 21 | 342 ± 42 | 262 ± 19 | 350 ± 32 | 257 ± 24$^x$ | 363 ± 48 | 286 ± 51 | 345 ± 37 | 288 ± 35 | 371 ± 33 | 305 ± 43 |
| 2 hr | 124 ± 8 | 155 ± 24 | 194 ± 12$^x$ | 154 ± 20 | 193 ± 21$^x$ | 185 ± 25 | 221 ± 33$^x$ | 160 ± 32 | 200 ± 32 | 172 ± 29 | 238 ± 53 |
| 3 hr | 87 ± 7 | 85 ± 6 | 102 ± 16 | 86 ± 4 | 105 ± 12 | 101 ± 4 | 145 ± 5$^z$ | 93 ± 9 | 102 ± 9 | 91 ± 12 | 137 ± 26 |
| ΔAUC (0-1) | | | | | | | | | | | |
| (mg·dL$^{-1}$·hr) | 195 ± 15 | 172 ± 21 | 95 ± 14$^y$ | 167 ± 20 | 91 ± 11$^y$ | 163 ± 23 | 100 ± 23$^x$ | 186 ± 20 | 113 ± 18$^x$ | 174 ± 17 | 117 ± 18$^x$ |
| (% of Control) | 100 ± 8 | 89 ± 11 | 49 ± 7$^y$ | 86 ± 10 | 47 ± 6$^y$ | 84 ± 12 | 51 ± 12$^x$ | 95 ± 10 | 58 ± 9$^x$ | 90 ± 9 | 60 ± 9$^x$ |

Mean ± S.E.M. (n = 5).
Difference from control:
$^x$P < 0.05;
$^y$P < 0.01;
$^z$P < 0.001.

Example 9

Figure 13:
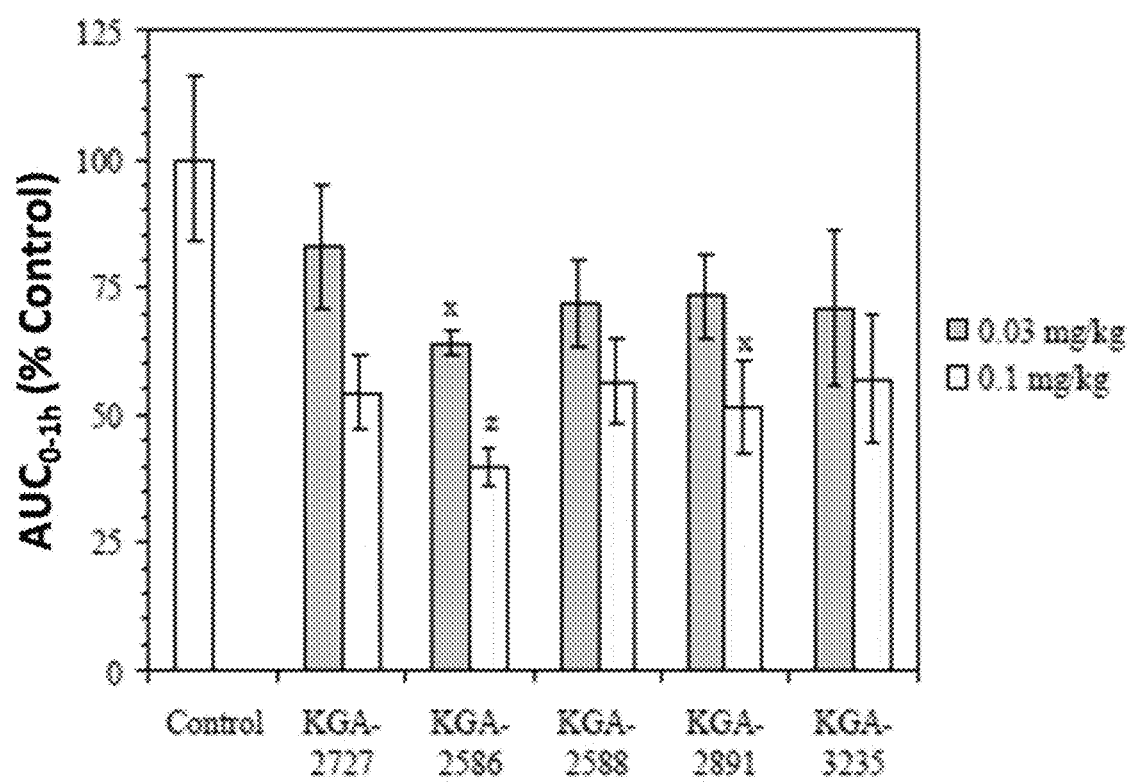
FIG. 13 shows the effects of SGLT1 inhibitors KGA-2727, KGA-2586, KGA-2588, KGA-2891 and KGA-3235 on $\Delta AUC_{(0-1\ h)}$ calculated from plasma glucose concentration after oral mixed-carbohydrate administration (2 g/kg) in STZ-induced diabetic rats. Data represent the mean±S.E.M. Difference from STZ-control: x, P<0.05; y, P<0.01; z, P<0.001.

Study in diabetic rats with mixed carbohydrates. Diabetic rats, induced by intravenous injection of streptozotocin (STZ; 40 mg/kg), were used to determining plasma glucose concentration (PG) 1 hr after oral mixed-carbohydrate tolerance test (OMCTT). Rats fasted overnight were administered the test substance solution (KGA-2727, KGA-2586, KGA-2588, KGA-2891 or KGA-3235, 0.03 and 0.1 mg/kg) or the vehicle (distilled water) orally at a dosing volume of 5 mL/kg, and were then immediately immediately administered 400 g/L mixed-carbohydrate (starch:sucrose:lactose=6:3:1) solution orally at a dosing volume of 5 mL/kg. Blood was collected via the caudal artery immediately before dosing and 0.5, 1, 2, and 3 hr after dosing. The glucose concentration measurement in plasma used Glucose CII-Test Wako kit (Wako Pure Chemicals Industries, Ltd., Osaka, Japan). The variables used for efficacy assessment were the measurement values of the plasma glucose concentration and the area under the curve for plasma glucose concentration through 1 hr after loading ($\Delta AUC_{0-1\ hr}$). The $\Delta AUC_{0-1\ hr}$ for plasma glucose was calculated based on the trapezoid method using the change of plasma glucose concentrations from pre-value (0 hr). KGA-2727, KGA-2586, KGA-2588, KGA-2891 and KGA-3235 inhibited PG elevation after glucose administration dose dependently (Table 10 and FIG. 13).

TABLE 10

| | Control | KGA-2727 | | KGA-2586 | | KGA-2588 | | KGA-2891 | | KGA-3235 | |
|---|---|---|---|---|---|---|---|---|---|---|---|
| | | 0.03 mg/kg | 0.1 mg/kg | 0.03 mg/kg | 0.1 mg/kg | 0.03 mg/kg | 0.1 mg/kg | 0.03 mg/kg | 0.1 mg/kg | 0.03 mg/kg | 0.1 mg/kg |
| Body weight (g) | 280 ± 11 | 283 ± 5 | 286 ± 3 | 295 ± 7 | 286 ± 6 | 302 ± 8 | 294 ± 5 | 292 ± 3 | 300 ± 9 | 298 ± 8 | 296 ± 8 |
| Plasma glucose (mg/dL) | | | | | | | | | | | |
| 0 hr | 123 ± 6 | 114 ± 7 | 124 ± 8 | 118 ± 8 | 126 ± 7 | 120 ± 3 | 123 ± 8 | 133 ± 6 | 124 ± 8 | 120 ± 9 | 128 ± 13 |
| 0.5 hr | 378 ± 34 | 317 ± 28 | 240 ± 17$^y$ | 269 ± 5$^y$ | 213 ± 11$^z$ | 291 ± 22 | 258 ± 25$^x$ | 327 ± 27 | 242 ± 29$^x$ | 289 ± 43 | 261 ± 44 |
| 1 hr | 267 ± 43 | 250 ± 30 | 248 ± 29 | 235 ± 8 | 215 ± 13 | 248 ± 17 | 224 ± 23 | 223 ± 14 | 226 ± 21 | 245 ± 28 | 234 ± 37 |
| 2 hr | 128 ± 27 | 114 ± 5 | 133 ± 4 | 112 ± 11 | 144 ± 12 | 109 ± 7 | 132 ± 4 | 119 ± 10 | 132 ± 15 | 129 ± 4 | 136 ± 16 |
| 3 hr | 110 ± 9 | 104 ± 7 | 106 ± 9 | 108 ± 10 | 108 ± 8 | 100 ± 6 | 114 ± 6 | 97 ± 5 | 114 ± 4 | 106 ± 4 | 98 ± 8 |

TABLE 10-continued

| | Control | KGA-2727 | | KGA-2586 | | KGA-2588 | | KGA-2891 | | KGA-3235 | |
|---|---|---|---|---|---|---|---|---|---|---|---|
| | | 0.03 mg/kg | 0.1 mg/kg | 0.03 mg/kg | 0.1 mg/kg | 0.03 mg/kg | 0.1 mg/kg | 0.03 mg/kg | 0.1 mg/kg | 0.03 mg/kg | 0.1 mg/kg |
| ΔAUC (0-1) | | | | | | | | | | | |
| (mg · dL$^{-1}$ · hr) | 163 ± 26 | 135 ± 20 | 89 ± 12 | 105 ± 4$^x$ | 65 ± 6$^z$ | 117 ± 14 | 93 ± 13 | 120 ± 13 | 84 ± 15$^x$ | 116 ± 25 | 93 ± 20 |
| (% of Control) | 100 ± 16 | 83 ± 12 | 55 ± 7 | 64 ± 2$^x$ | 40 ± 4$^z$ | 72 ± 9 | 57 ± 8 | 73 ± 8 | 52 ± 9$^x$ | 71 ± 15 | 57 ± 12 |

Mean ± S.E.M. (n = 5).
Difference from control:
$^x$P < 0.05;
$^y$P < 0.01;
$^z$P < 0.001.

Example 10

Study in mice. Adult male mice (C57BL/6-Tyrc-Brd) were fed a high glucose diet for 6 days prior oral glucose tolerance test. Mice were treated once a day for 5 days with either LX2761 (0.009, 0.012, 0.015, 0.05 or 0.15 mg/kg) or vehicle by oral administration. Mice were fed ad lib for 15 hours prior to the final dose of LX2761 or vehicle and the oral glucose tolerance test. Glucose levels were determined prior to and following the oral glucose challenge. LX2761 doses of ≤0.15 mg/kg can decrease OGTT glucose excursions in mice. LX2761 decreased oral glucose excursions during OGTT. These results from these tests are shown in FIG. 2 of in the journal article, Powell et al. *J Pharmacol Exp Ther.* 2017 362(1): 85-97, which is herein incorporated by reference in its entirety. LX2761 doses less than or equal to 0.15 mg/kg significantly decreased OGTT glucose excursions.

Example 11

Pharmaceutical formulations. Exemplary oral pharmaceutical formulations are comprised of tablets 2.5 mg, 5 mg and 10 mg that are white to slightly yellowish white film-coated tablets with an oval shape of 8 mm×4.5 mm. The qualitative compositions of the tablet excipients are shown in Table 11 (below). The container closure system is tight sealed container.

TABLE 11

| Material | Specification | Commercial Grade | Supplier | Function |
|---|---|---|---|---|
| KGA-3235 Sebacate | — | — | Katayama Seiyakusyo | Active drug substance |
| D-Mannitol | USP, EP, JP | PEARLITOL 100SD | Merck Millipore | Filler |
| Corn Starch | USP, EP, JP | — | NIHON SHOKUHIN KAKO | Filler |
| Low-substituted Hydroxypropyl Cellulose | NF, JP | L-HPC (LH-11) | Shin-Etsu Chemical | Disintegrant |
| Magnesium Stearate | NF, EP, JP | Vegetable | Taihei Chemical Industrial | Lubricant |
| Hypromellose | USP, EP, JP | TC-5R | Shin-Etsu Chemical | Coating agent |
| Hydroxypropyl Cellulose | NF, EP, JP | HPC-SL | Nippon Soda | Coating agent |
| Talc | NF, EP, JP | Crown talc | Matsumura Sangyo | Coating agent |
| Carnauba Wax | NF, EP, JP | Powder | Nihon Wax | Brightening agent |

The quantitative composition of the tablet excipients is presented in Table 12.

TABLE 12

| | mg per tablet | |
|---|---|---|
| Component | 2.5 mg | 5 mg |
| KGA-3235 Sebacate (free form) | 2.95 (2.5) | 5.9 (5) |
| D-Mannitol | 76.05 | 78.1 |
| Corn Starch | 10 | 10 |
| Low-substituted Hydroxypropyl Cellulose | 10 | 5 |
| Magnesium Stearate | 1 | 1 |
| Hypromellose | 1.35 | 1.35 |
| Hydroxypropyl Cellulose | 1.35 | 1.35 |
| Talc | 0.3 | 0.3 |
| Carnauba Wax | Trace (0.02) | Trace (0.02) |
| Total | 103 $^{a)}$ | 103 $^{a)}$ |

What is claimed:

1. A method of treating a subject with post-prandial hypoglycemia associated with a gastric surgery, comprising the step of orally administering a sodium-dependent glucose transporter (SGLT)1 inhibitor compound of Formula I or Formula II, or a pharmaceutically acceptable salt thereof, to said subject, wherein the compound of Formula I is:

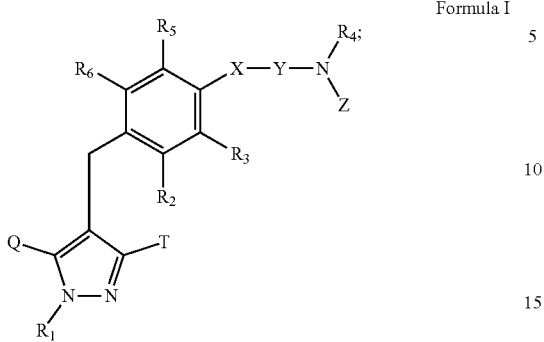

Formula I wherein
R₁ represents H, or an optionally substituted $C_{1-6}$ alkyl group;
one of Q and T represents a group:

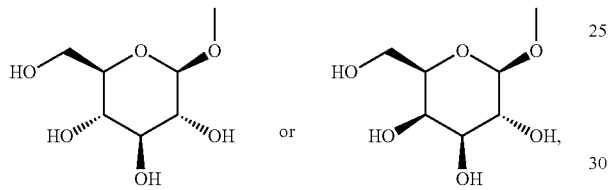

while the other represents a $C_{1-6}$ alkyl group, a halo($C_{1-6}$ alkyl) group, a $C_{1-6}$ alkoxy-substituted ($C_{1-6}$ alkyl) group or a $C_{3-7}$ cycloalkyl group;
R₂ represents a hydrogen atom, a halogen atom, a hydroxy group, a $C_{1-6}$ alkyl group, a $C_{1-6}$ alkoxy group, a $C_{1-6}$ alkylthio group, a halo($C_{1-6}$ alkyl) group, a halo($C_{1-6}$ alkoxy) group, a $C_{1-6}$ alkoxy-substituted ($C_{1-6}$ alkoxy) group, a $C_{3-7}$ cycloalkyl-substituted ($C_{2-6}$ alkoxy) group or -A-R$^A$ in which A represents a single bond, an oxygen atom, a methylene group, an ethylene group, —OCH₂— or —CH₂O—; and R$^A$ represents a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkyl group, a $C_{1-6}$ alkoxy group, a $C_{2-6}$ alkenyloxy group, a halo($C_{1-6}$ alkyl) group, a hydroxy($C_{1-6}$ alkyl) group, a carboxy group, a $C_{2-7}$ alkoxycarbonyl group, a cyano group and a nitro group, or a heteroaryl group which may have a substituent selected from the group consisting of a halogen atom and a $C_{1-6}$ alkyl group;
X represents a single bond, an oxygen atom or a sulfur atom;
Y represents a $C_{1-6}$ alkylene group which may be substituted by a hydroxy group or a $C_{2-6}$ alkenylene group;
Z represents —R$^B$, —COR$^C$, —SO₂R$^C$, —CON(R$^D$)R$^E$, —SO₂NHR$^F$ or —C(=NR$^G$)N(R$^H$)R$^I$; R$^C$ represents an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), wherein substituent group (i) consists of:
a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON(R$^J$)R$^K$ in which R$^J$ and R$^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of RJ and RK bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent;
R₄, R$^B$, R$^D$, R$^E$ and R$^F$ are the same or different, and each represents a hydrogen atom, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, or a $C_{1-6}$ alkyl group which may have the same or different 1 to 5 groups selected from the following substituent group (i), wherein substituent group (i) consists of:

a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON($R^J$)$R^K$ in which $R^J$ and $R^K$ are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of RJ and RK bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl ($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group, and a $C_{1-4}$ aromatic cyclic amino group which may have a $C_{1-6}$ alkyl group as a substituent, or both of $R_4$ and $R^B$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl ($C_{1-6}$ alkyl) group, a hydroxy($C_{1-6}$ alkyl) group and a $C_{1-6}$ alkylsulfonylamino-substituted ($C_{1-6}$ alkyl) group, or both of $R^D$ and $R^E$ bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted ($C_{1-6}$ alkyl) group; $R^G$, $R^H$ and $R^I$ are the same or different, and each represents a hydrogen atom, a cyano group, a carbamoyl group, a $C_{2-7}$ acyl group, a $C_{2-7}$ alkoxycarbonyl group, an aryl($C_{2-7}$ alkoxycarbonyl) group, a nitro group, a $C_{1-6}$ alkylsulfonyl group, a sulfamide group, a carbamimidoyl group, or a $C_{1-6}$ alkyl group which may have the same or different 1 to 5 groups selected from the following substituent group (i) wherein substituent group (i) consists of:

a hydroxy group, a $C_{1-6}$ alkoxy group, a $C_{1-6}$ alkylthio group, an amino group, a mono or di($C_{1-6}$ alkyl)amino group, a mono or di[hydroxy($C_{1-6}$ alkyl)]amino group, an ureido group, a sulfamide group, a mono or di($C_{1-6}$ alkyl)ureido group, a mono or di($C_{1-6}$ alkyl)sulfamide group, a $C_{2-7}$ acylamino group, a $C_{1-6}$ alkylsulfonylamino group, a $C_{1-6}$ alkylsulfonyl group, a carboxy group, a $C_{2-7}$ alkoxycarbonyl group, —CON($R^J$)$R^K$ in which $R^J$ and $R^K$ (are the same or different, and each represents a hydrogen atom or a $C_{1-6}$ alkyl group which may have the same or different 1 to 3 substituents selected from the group consisting of a hydroxy group, an amino group, a mono or di($C_{1-6}$ alkyl)amino group, a mono or di[hydroxy($C_{1-6}$ alkyl)]amino group, an ureido group, a mono or di($C_{1-6}$ alkyl)ureido group, a $C_{2-7}$ acylamino group, a $C_{1-6}$ alkylsulfonylamino group and a carbamoyl group, or both of RJ and RK bind together with the neighboring nitrogen atom to form a $C_{2-6}$ cyclic amino group which may have a substituent selected from the group consisting of a hydroxy group, a carbamoyl group, a $C_{1-6}$ alkyl group, an oxo group, a carbamoyl ($C_{1-6}$ alkyl) group, a hydroxy($C_{1-6}$ alkyl) group and a $C_{1-6}$ alkylsulfonylamino-substituted ($C_{1-6}$ alkyl) group, an aryl($C_{1-6}$ alkoxy) group which may have the same or different 1 to 3 substituents selected from the group consisting of a halogen atom, a hydroxy group, an amino group, a $C_{1-6}$ alkyl group and a $C_{1-6}$ alkoxy group on the ring, an aryl($C_{1-6}$ alkylthio) group which may have the same or different 1 to 3 substituents selected from the group consisting of a halogen atom, a hydroxy group, an amino group, a $C_{1-6}$ alkyl group and a $C_{1-6}$ alkoxy group on the ring, a $C_{3-7}$ cycloalkyl group, a $C_{2-6}$ heterocycloalkyl group, an aryl group which may have the same or different 1 to 3 substituents selected from the group consisting of a halogen atom, a hydroxy group, an amino group, a $C_{1-6}$ alkylsulfonylamino group, a $C_{1-6}$ alkyl group and a $C_{1-6}$ alkoxy group, a heteroaryl group which may have a substituent selected from the group consisting of a halogen atom, an amino group and a $C_{1-6}$ alkyl group, a $C_{2-6}$ cyclic amino group which may have a substituent selected from the group consisting of a hydroxy group, a carbamoyl group, a $C_{1-6}$ alkyl group, an oxo group, a carbamoyl($C_{1-6}$ alkyl) group, a hydroxy($C_{1-6}$ alkyl) group and a $C_{1-6}$ alkylsulfonylamino-substituted (C$_{1-6}$ alkyl) group, and a C$_{1-4}$ aromatic cyclic amino group which may have a C$_{1-6}$ alkyl group as a substituent,
or both of R$^G$ and R$^H$ bind to form an ethylene group, or both of R$^H$ and R$^I$ bind together with the neighboring nitrogen atom to form a C$_{2-6}$ cyclic amino group which may have a substituent selected from the group consisting of a hydroxy group, a carbamoyl group, a C$_{1-6}$ alkyl group, an oxo group, a carbamoyl(C$_{1-6}$ alkyl) group, a hydroxy(C$_{1-6}$ alkyl) group and a C$_{1-6}$ alkylsulfonylamino-substituted (C$_{1-6}$ alkyl) group;
R$_3$, R$_5$ and R$_6$ are the same or different, and each represents a hydrogen atom, a halogen atom, a C$_{1-6}$ alkyl group or a C$_{1-6}$ alkoxy group;
and wherein the compound of Formula II is:

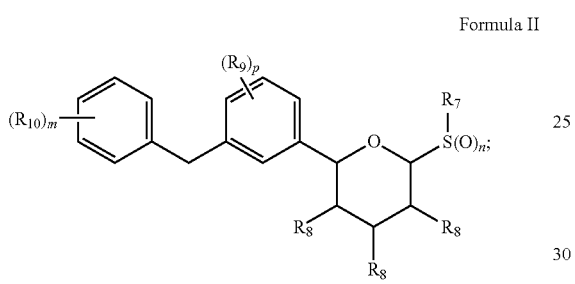

Formula II wherein
R$_7$ is hydrogen or optionally substituted C$_{1-10}$-alkyl, C$_{1-5}$-cycloalkyl, or 5-membered heterocycle, which optional substitution is with one or more R$_{7A}$; each R$_{7A}$ is independently amino, ester, amide, thiol, carboxylic acid, cyano, halo, hydroxyl, or optionally substituted C$_{1-4}$-alkoxy, C$_{1-5}$-cycloalkyl, or 5-membered heterocycle, which optional substitution is with one or more R$_{7B}$; each R$_{7B}$ is independently C$_{1-4}$-alkyl, halo, or hydroxyl; n is 0, 1, or 2;
each R$_8$ is independently F or OR$_{8A}$, wherein each R$_{8A}$ is independently hydrogen, C$_{1-4}$-alkyl, or acyl;
each R$_9$ is independently halo, hydroxyl, or optionally substituted C$_{1-10}$-alkyl or C$_{1-10}$-alkoxy, which optional substitution is with one or more R$_{9A}$; each R$_{9A}$ is independently amino, ester, amide, thiol, carboxylic acid, cyano, halo, hydroxyl, or optionally substituted C$_{1-4}$-alkoxy, C$_{1-5}$-cycloalkyl, or 5-membered heterocycle, which optional substitution is with one or more R$_{9B}$; each R$_{9B}$ is independently C$_{1-4}$-alkyl, amino, cyano, halo, or hydroxyl;
p is 0, 1, or 2;
each R$_{10}$ is independently R$_{10A}$, —N(R$_{10A}$)(R10B), —OR$_{10A}$, —SR$_{10A}$, —S(O)R$_{10A}$, or —S(O)2R$_{10A}$; R$_{10A}$ is optionally substituted C$_{4-20}$-alkyl or 4-20-membered heteroalkyl, which optional substitution is with one or more R$_{10C}$, and which is optionally attached to another R$_{10A}$ moiety to provide a dimer or trimer; R$_{10B}$ is hydrogen or R$_{10A}$; each R$_{10C}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, thiourea, urea, or X$_1$, X$_1$-L$_1$-X$_2$, or X$_1$-L$_1$-X$_2$-L$_2$-X$_3$, wherein each of X$_1$, X$_2$ and X$_3$ is independently optionally substituted C$_{1-4}$-alkyl, C$_{1-6}$-cycloalkyl, 5- or 6-membered heterocycle, or aryl, which optional substitution is with one or more Rim, and each of L$_1$ and L$_2$ is independently optionally substituted C$_{1-6}$-alkyl or 1-10-membered heteroalkyl, which optional substitution is with one or more of R$_{10E}$; each R$_{10D}$ is independently R$_{10E}$ or C$_{1-6}$-alkyl optionally substituted with one or more of R$_{10E}$; each R$_{10E}$ is independently amino, amido, azo, carbonyl, carboxyl, cyano, formyl, guanidino, halo, hydroxyl, imido, imino, isothiocyanate, nitrile, nitro, nitroso, nitroxy, oxo, sulfanyl, sulfinyl, sulfonyl, thial, thiocyanate, thione, or urea; and m is 1, 2 or 3;
wherein the SGLT1 inhibitor compound inhibits SGLT1 in the intestinal lumen of the subject.

2. The method of claim 1, wherein the post-prandial hypoglycemia is associated with gastric surgery, wherein the gastric surgery is selected from the group consisting of gallbladder surgery, stomach cancer surgery (gastrectomy), colorectal cancer; esophageal cancer, inflammatory bowel disease surgery, bariatric surgery, gastric bypass surgery, Roux-en-Y surgery, and sleeve gastrectomy.

3. The method of claim 1, wherein the post-prandial hypoglycemia is associated with Nissen fundoplication.

4. The method of claim 1, wherein the SGLT1 inhibitor compound is selected from the group consisting of:

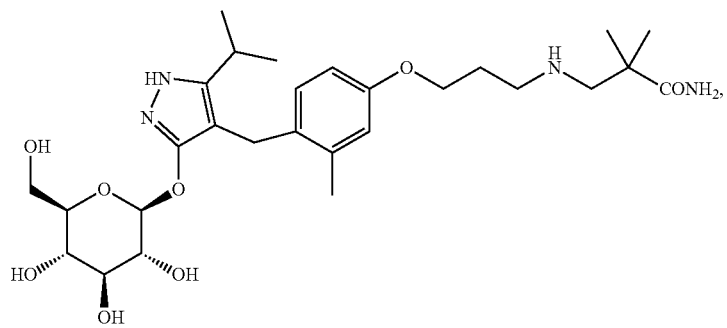

KGA-3235 Mizagliflozin

-continued
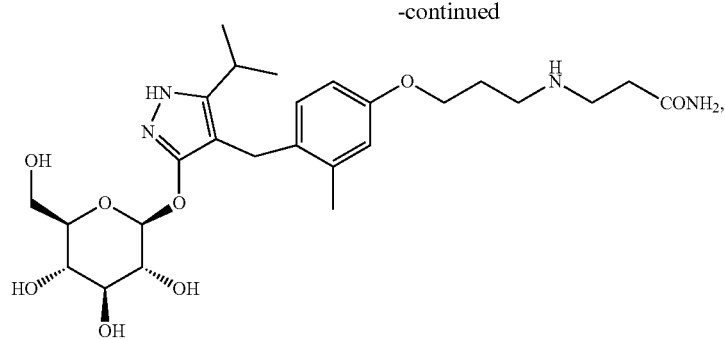
KGA-2727
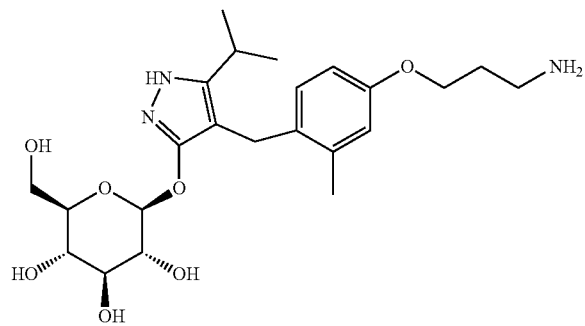
KGA-2586
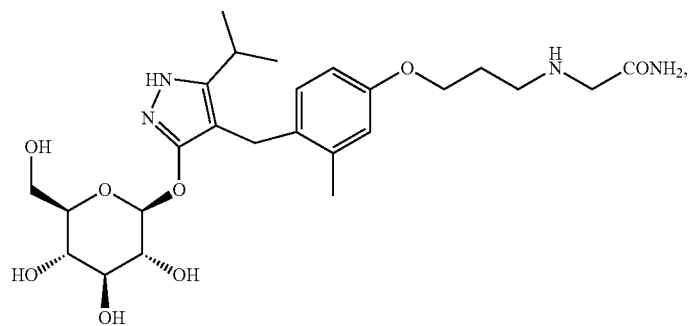
KGA-2588
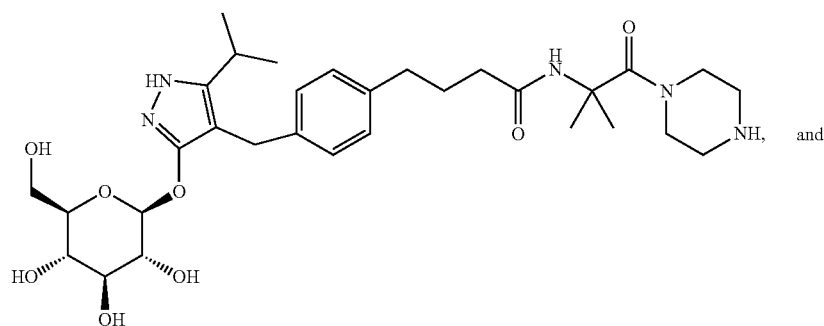
KGA-2891

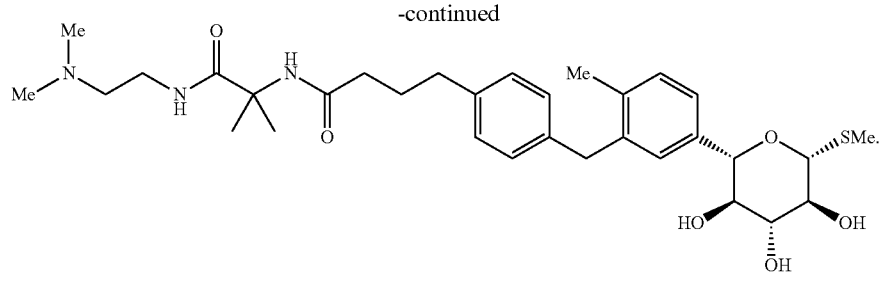

LX2761

5. The method of claim 4, wherein the SGLT1 inhibitor compound is selected from mizagliflozin or LX2761.

6. The method of claim 5, wherein the SGLT1 inhibitor compound is mizagliflozin.

7. The method of claim 5, wherein the SGLT1 inhibitor is LX2761.

8. The method of claim 1, wherein the pharmaceutical salt of the SGLT1 inhibitor compound is selected from monosebacate and hemifumarate dehydrate of the compound.

9. The method of claim 1 wherein the SGLT1 inhibitor compound, or pharmaceutically acceptable salt thereof, is administered as a unit dose of, from about 0.1 mg to about 20 mg, one to three times a day.

10. The method of claim 1, wherein the SGLT1 inhibitor compound, or pharmaceutically acceptable salt thereof, is administered in combination with at least one alpha-glucosidase inhibitor or glucagon-like peptide (GLP)-1 receptor antagonist.

11. The method of claim 10, wherein the alpha-glucosidease inhibitor is selected from the group consisting of acarbose, voglibose, and miglitol.

12. The method of claim 10, wherein the GLP-1 receptor-antagonist is exendin 9-39.

13. The method of claim 1 wherein the SGLT1 inhibitor compound, or pharmaceutically acceptable salt thereof, is administered before a meal.

14. The method of claim 2, wherein the gastric surgery is Roux-en-Y surgery.

15. The method of claim 2, wherein the gastric surgery is sleeve gastrectomy.

* * * * *